(12) United States Patent
Cohen

(10) Patent No.: US 9,693,843 B2
(45) Date of Patent: Jul. 4, 2017

(54) STRAINER/FILTER UNIT FOR AN ASPIRATING FILTRATION SYSTEM AND METHOD THEREOF

(76) Inventor: Howard Cohen, Hudson County, NJ (US)

( * ) Notice: Subject to any disclaimer, the term of this patent is extended or adjusted under 35 U.S.C. 154(b) by 1062 days.

(21) Appl. No.: 12/454,771

(22) Filed: May 22, 2009

(65) Prior Publication Data

US 2010/0297577 A1    Nov. 25, 2010

(51) Int. Cl.
*A61C 17/06* (2006.01)
*A61C 17/14* (2006.01)
*A61M 1/00* (2006.01)

(52) U.S. Cl.
CPC ......... *A61C 17/046* (2013.01); *A61M 1/0056* (2013.01); *A61C 17/043* (2013.01)

(58) Field of Classification Search
CPC ........ B01D 29/01; B01D 29/21; B01D 35/30; B01D 35/143; A61C 17/04; A61C 17/043; A61C 17/046
USPC ............ 433/90–98, 215; 210/97, 136, 416.1, 210/258, 533, 808; 422/28, 401
See application file for complete search history.

(56) References Cited

U.S. PATENT DOCUMENTS

| | | | |
|---|---|---|---|
| 3,758,950 A * | 9/1973 | Krouzian | A61C 17/043 433/91 |
| 3,890,712 A | 6/1975 | Lopez | |
| 4,054,998 A * | 10/1977 | Hesselgren | A61C 17/046 422/28 |
| 4,058,896 A | 11/1977 | Moore | |
| 4,265,621 A | 5/1981 | McVey | |
| 4,464,254 A | 8/1984 | Dojki et al. | |
| 5,078,603 A | 1/1992 | Cohen | |
| 5,195,952 A * | 3/1993 | Solnit | A61C 17/043 433/91 |
| 5,464,397 A * | 11/1995 | Powers, Jr. | A61M 1/0039 433/95 |
| 5,630,939 A | 5/1997 | Bulard et al. | |
| 5,741,134 A * | 4/1998 | Davis | A61C 17/043 210/446 |
| 5,779,649 A | 7/1998 | Herbert | |
| 5,855,478 A * | 1/1999 | Van | A61C 17/043 433/95 |
| 5,922,614 A | 7/1999 | Cesarczyk | |
| 6,102,699 A * | 8/2000 | Galehr | A61C 5/062 433/90 |

(Continued)

OTHER PUBLICATIONS

American Dental Association, Summary of Recent Study of Dental Amalgam in Wastewater, American Dental Association Article, Aug. 5, 2005, Chicago, Illinois, U.S.A.

(Continued)

*Primary Examiner* — Matthew Nelson
(74) *Attorney, Agent, or Firm* — Walter J. Tencza, Jr.

(57) ABSTRACT

A strainer/filter unit for effectively collecting solid, liquid or gaseous substances at the source and the method of using the strainer/filter unit. The strainer/filter unit includes a housing, a one-way valve at one end of the housing, and a filter having a certain depth and thickness within the housing. The filter is formed from a plurality of layers of material with pores such that pores of one layer partially overlap pores of subsequent adjacent layers. Matters entering the strainer/filter unit are collected in the filter while travelling through filter via a tortuous path.

54 Claims, 28 Drawing Sheets

(56) References Cited

U.S. PATENT DOCUMENTS

| | | | | |
|---|---|---|---|---|
| 6,183,254 B1* | 2/2001 | Cohen | A61C 17/043 | 433/92 |
| 6,302,692 B1* | 10/2001 | Pond | A61C 1/0076 | 433/100 |
| 6,395,551 B1* | 5/2002 | Kipke | G01N 31/226 | 422/401 |
| 6,428,316 B1* | 8/2002 | Rodriquez | A61C 17/046 | 433/92 |
| 6,946,069 B2* | 9/2005 | Chilibeck | A61C 17/046 | 210/258 |
| 7,214,059 B2 | 5/2007 | Takahashi | | |
| 7,588,732 B2* | 9/2009 | Buss | A61M 1/0084 | 210/406 |
| 2001/0041323 A1* | 11/2001 | Castellini | A61C 1/0076 | 433/84 |
| 2003/0219696 A1* | 11/2003 | Moreland | A61C 17/043 | 433/95 |
| 2003/0226857 A1* | 12/2003 | Bibbo | B01F 15/0263 | 222/148 |
| 2004/0115590 A1 | 6/2004 | Takahashi | | |
| 2004/0197732 A1* | 10/2004 | Sullman | A61C 17/043 | 433/94 |
| 2005/0072725 A1* | 4/2005 | Swanson | B01D 27/02 | 210/289 |
| 2005/0279678 A1* | 12/2005 | Carlson | A61C 17/046 | 210/97 |
| 2005/0282107 A1* | 12/2005 | Stone | A61C 17/046 | 433/92 |
| 2006/0024641 A1* | 2/2006 | Mahlmann | A61C 17/043 | 433/96 |
| 2006/0068030 A1* | 3/2006 | Jensen | A61K 33/10 | 424/687 |
| 2007/0210011 A1* | 9/2007 | Hook | B01D 39/08 | 210/767 |
| 2008/0257815 A1* | 10/2008 | McCary | A61C 17/04 | 210/416.1 |
| 2009/0211963 A1* | 8/2009 | Murray | B01D 21/0012 | 210/433.1 |
| 2012/0043475 A1* | 2/2012 | Ahn | A61B 6/04 | 250/453.11 |

OTHER PUBLICATIONS

Ulla Jacobsson-Hunt DDS, DMD, Amalgam and Mercury in the Dental Setting and the Efficiency of Amalgam Separators, Master of Science Thesis, Linkopings University, Jun. 5, 2007, Norrkoping, Sweden.

* cited by examiner

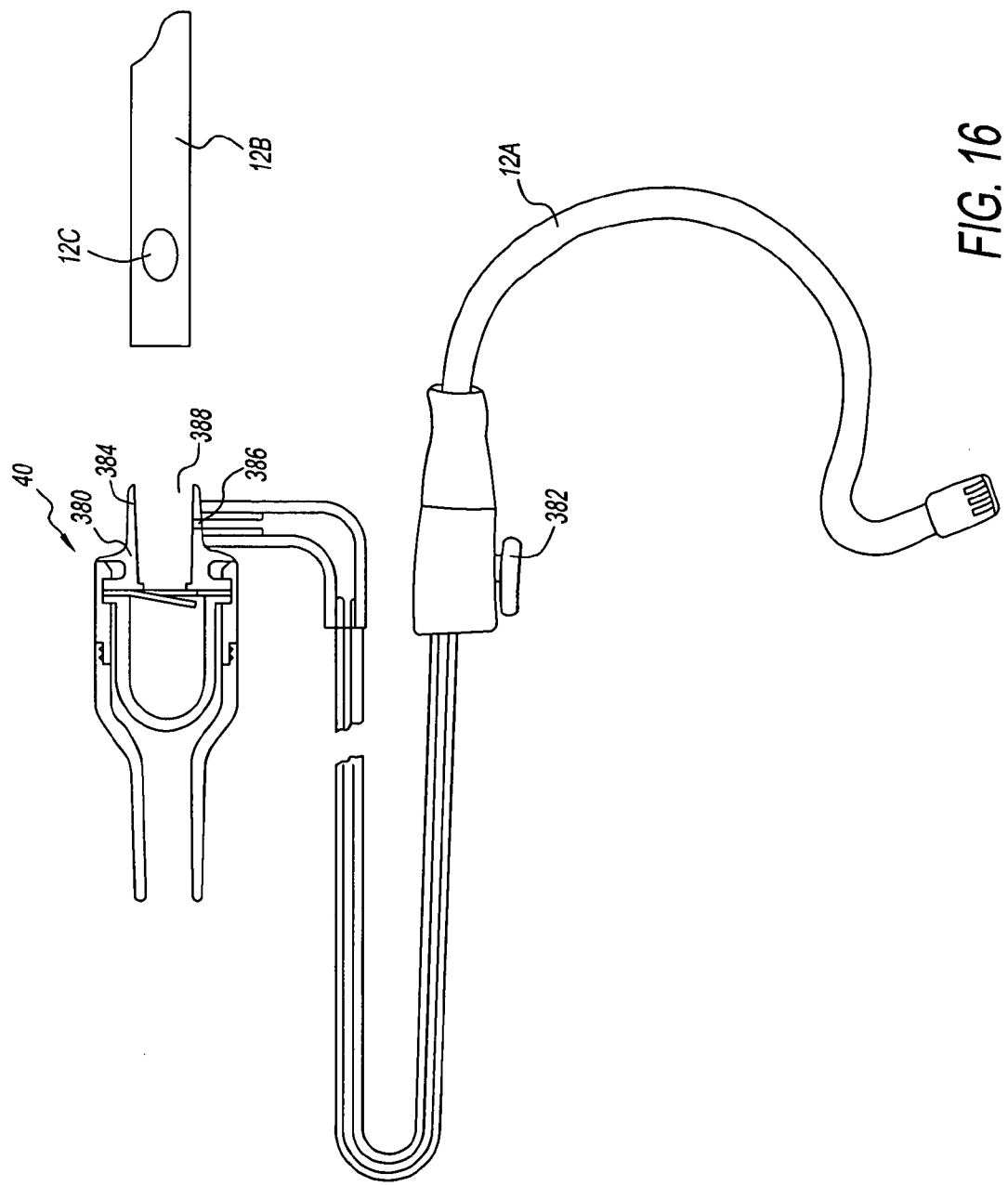

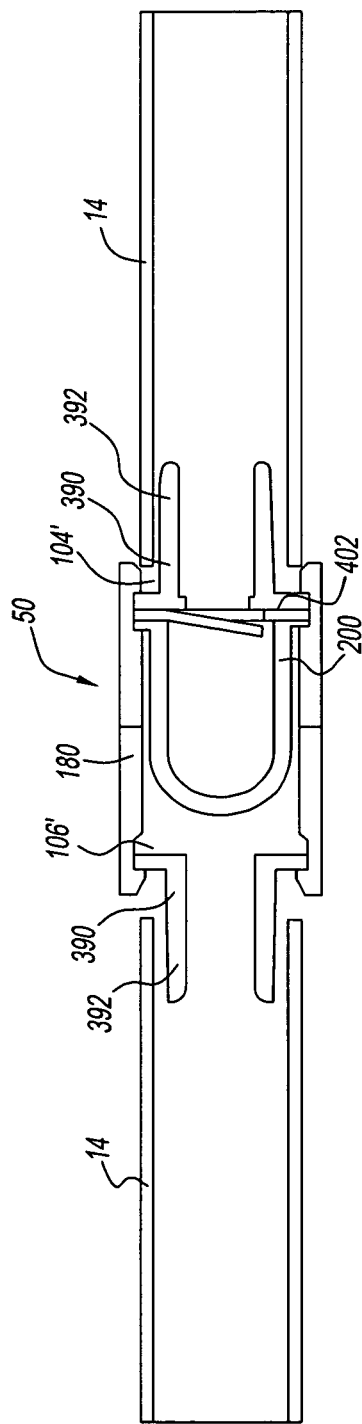
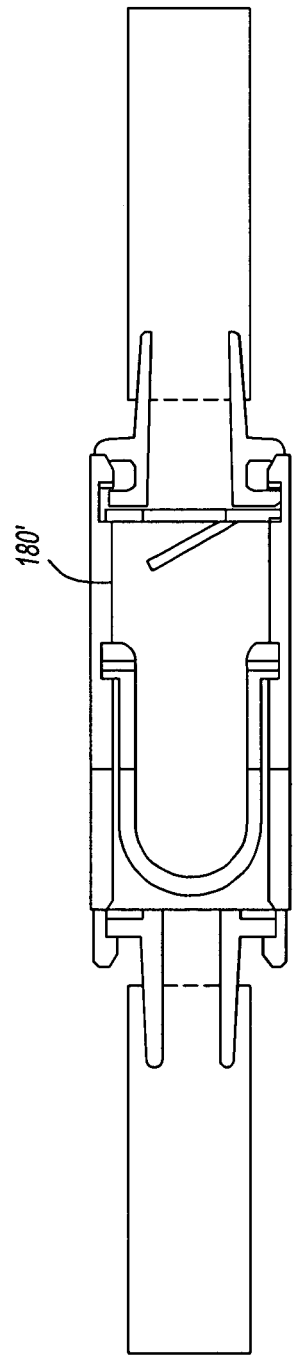
FIG. 17A
FIG. 17B

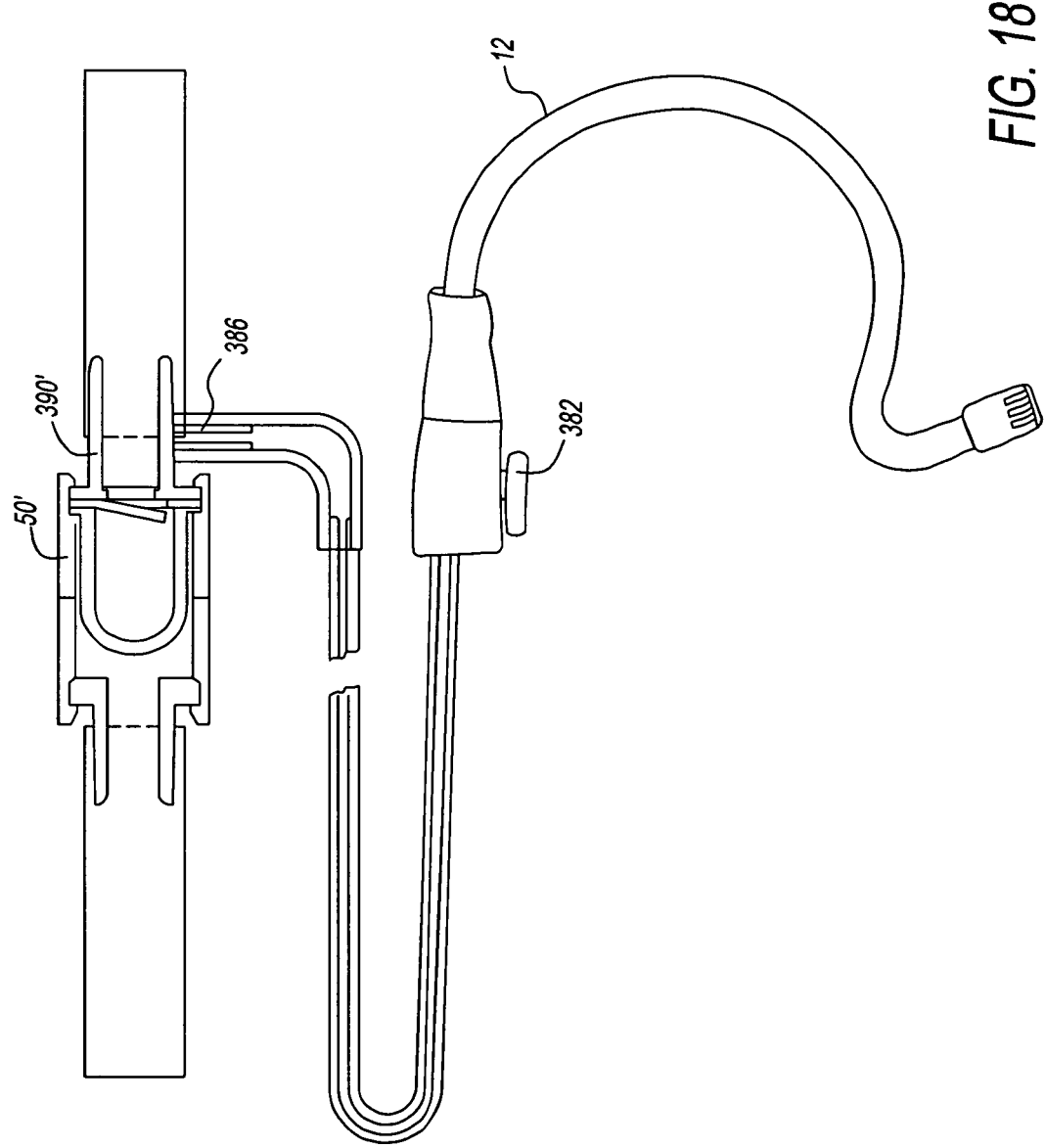

STRAINER/FILTER UNIT FOR AN ASPIRATING FILTRATION SYSTEM AND METHOD THEREOF

FIELD OF THE INVENTION

The invention relates to an apparatus that collects solid waste at the source and the method thereof. In particular, a strainer/filter unit having an anti-retraction valve and a filter with an appropriate depth and thickness such that solid matters are collected while travelling through a tortuous path and for use in connection with a vacuum-operated type aspirating system that aspirates liquids, solids and gases, and prevents the back-flow of liquids, solids and gases. The present invention is particularly useful in the dental field.

BACKGROUND OF THE INVENTION

Dental procedures can cause solid matter (e.g. bone chips, tooth particles, tissue fragments, pieces of amalgam, mercury, other toxic or hazardous chemicals, composite residual, fragments of porcelain restoration, zirconium, aluminum oxide, and cleaning paste that contains silica, etc.) to enter fluids (e.g. saliva, blood, and cooling water) that are present in the patients' mouth. The solid matter is removed from the mouth to prevent the patient from swallowing or aspirating it and prevent it from entering the suction or water waste lines. Removal of the solid matter necessarily entails removal of the fluids and gases as well. When such fluids and gases are withdrawn from the patient's mouth (as by a vacuum powered saliva ejector or a high-volume aspirator/evacuator (HVE)), this solid matter can cause difficulties for the dentist and for the patient especially when the patient is anesthetized. Additionally, the solid matter can clog the vacuum/suction system and water waste line so as to cause it to malfunction. Another such difficulty is that the solid, liquid and gaseous matters can be incorporated in an aerosol created during a dental procedure and the build up of the solid matter can occur on the inner surfaces of the vacuum/suction and dental unit lines and suction and water waste lines, thereby forming an area for the growth of bio-film that in turn promotes the growth of bacteria. For these reasons, it is known to provide a variety of strainer/filter units behind the ejector or high volume evacuator (HVE) aspirator and in the dental operatory unit as well as in the suction lines of a vacuum system. Dental unit trap, such as a chairside or inline trap, can be used in the cuspidor, suction and water waste lines and suction pump. However, such trap cannot effectively filter small amalgams and other solid, liquid or gaseous particles and unnecessarily expose dental professional and patients to amalgam (and its mercury vapors and methyl mercury) in the operatory. The strainer/filter unit for the filtration system of the present invention separates the solid matter from the fluids, thereby preventing amalgam and other particles from entering the dental unit, pipelines of the suction system and suction pumps that are connected to the water waste lines without significantly adversely affecting the suction flow. Conventionally, the saliva ejector or HVE aspirator and source amalgam separator with a strainer/filter unit is disposable. Optionally, the strainer/filter unit of the present invention that collects solid, liquid and gaseous waste may not be entirely disposable or parts of it may be sterilized and re-used.

At the present time, amalgam particles are comprised of approximately fifty percent (50%) mercury and its disposal is of great concern to the Environmental Protection Agency (EPA) of the United States. Several states, cities and local townships have enacted laws providing for mandatory guidelines that now require dentists and endodontists who perform procedures involving amalgam to have a device called an amalgam separator. Current amalgam separators are solid waste collectors and are connected to the terminal aspect of the suction line at their inlet port and to the motorized suction pump at its outlet port. There are four general types of amalgam separators—sedimentation, filtration, centrifuge and a combination of two or more of the foregoing types. Existing amalgam separators typically require professional installation and are costly to install and maintain. For example, the building or dental office may need to be reconfigured to accommodate the currently available amalgam separators and the amalgam separators and suction system needs to be routinely cleaned.

The amalgam separator must conform to the International Standards Organization (ISO) 11143 Standard so as to collect ninety-five percent (95%) of amalgam waste generated as being advocated by "Best Management Practice" of the American Dental Association to minimize amalgam waste particles from entering the water waste lines of the sewage system. Most recently, New York State (NYS) has enacted mandatory regulations for dentists who perform procedures involving amalgam to capture ninety-nine percent (99%) of amalgam particles generated. Other states also have regulations or are contemplating regulations concerning amalgam or dental waste collection.

A Master of Science Thesis, Environmental Science Programme 2007, by Ulla Jacobson-Hunt, DDS, DMD, from Sweden, entitled "Amalgam and Mercury in the Dental Setting and the Efficiency of Amalgam Separators" points to the deficiencies of prior art amalgam separators. The author reveals on page two that "in a clinical setting amalgam separators are less effective, and only provide 60% and up in collecting amalgam waste from a dental facility." The author concludes on page 32 of her thesis "that the clinical efficiency of the amalgam separators currently in Sweden are not meeting the ISO 11143 Standard" and she further infers that more studies are needed as to the clinical efficiency as the ISO 11143 Standard was solely based upon laboratory testing of amalgam separators. It is interesting to note that Sweden has recently proposed banning the use of amalgam in its country. If the U.S. is to ban its use, it is estimated to cost the public's dental expenses of $8.2 billion during the first year. To trained investigators, the performance of mandatory devices should undergo both rigid clinical and laboratory testing and this applies most appropriately to amalgam separators to substantiate their efficacy and claims made for these devices. Laws are being enacted mandating the use of amalgam separators based upon faulty science and such laws are a burden to those dentists who perform procedures involving amalgam as well as being misleading to environmentalists, the EPA and waste water and sludge treatment plants.

Other investigators have noted that clinical evaluation of existing amalgam separators would be difficult to perform and an article by the American Dental Association (ADA) dated Aug. 5, 2005, entitled "Summary of Recent Study of Dental Amalgam in Waste Water" states that "measuring the exact amount of amalgam waste being generated and discharged from a dental office is a very difficult task. The discharge of amalgam waste into sewerage systems is complicated by the fact that this waste is generated on an intermittent basis with huge day-to-day and even minute-to-minute variations. Methods such as sampling from drain or sewer lines, or even collecting total waste over several days show huge variations that are difficult to extrapolate into total waste generated over a year. For these reasons, sampling dental office wastewater discharge does not provide either an accurate or reliable estimate of discharge."

It is important to note that, often times, upon completion of placement or removal of amalgam, the vacuum valves of the HVE and the saliva ejector holders are shut off. This results in amalgam particles possibly settling within the dental units and the pipelines of the suction system and water waste lines and become embedded within the biofilm of the dental units and pipelines of the suction system and water waste lines so as to prevent the amalgam particles from reaching the attached conventional amalgam separator. Over a period of time, a narrowing of the lumen of these lines may occur. In such a situation the use of disinfectants such as sodium hypochlorite will change the accumulated amalgam particles into methyl mercury which is considered toxic and the most hazardous form of amalgam waste.

Further, it is important to note that when the vacuum valves, air compressor for tools and water lines are shut off after a procedure for a patient, microbial contamination of the dental unit and water lines can occur due to the "suck back" phenomenon, which may be partially embedded in an existing biofilm. When air compresses, water condensation forms in the pipes. When the suction force, air compressor and water are shut off, air (and all airborne contaminants) from the environment are drawn into the valves, pipes and water lines, respectively. Upon the subsequent usage of the vacuum valves, air compressor and water lines, the liquids, solids and airborne (or vapor) contaminants come into contact with the next patient. This "suck back" phenomenon increases the likelihood of dental acquired infections.

All existing amalgam separators must be clinically considered to be inadequate in meeting the ISO Standard 11143 as they are not removing 95% of the amalgam particles generated. Another problem exists with prior art amalgam separators in that it is necessary to maintain a pH in the range of 5 to 10 within the dental units and pipelines of the suction system. Although bleach is typically used in dental procedures (to sterilize and disinfect root canal or to etch the tooth for bonding or tooth whitening or bleaching), bleach cannot be used with existing amalgam separators because it would adversely affect the pH level in the pipelines of the suction system. A pH below or above the 5 to 10 range may adversely affect the amalgam particles attached to the biofilm or amalgam particles resulting from a procedure involving amalgam so as to possibly cause the release of mercury vapors or result in the production of methyl mercury that is toxic and considered the most hazardous particle form from amalgam.

Existing strainer/filter units have a number of disadvantages. First, existing strainer/filter units within the dental unit and suction lines of saliva ejectors and HVE aspirators are difficult, if not impossible, to sterilize. The Food and Drug Administration (FDA) regulations in the United States do not require the strainer/filter units to be sterile as well as the saliva ejectors and aspirators and they need only be cleaned, which in itself is labor intensive and not cost effective. Even if a particular dentist is motivated to sterilize a strainer/filter unit and aspirator before connecting them to the dental unit and vacuum systems, existing strainer/filter units and aspirators can neither be easily emptied nor cleaned and sterilized. Hence, the strainer/filter unit and aspirator/HVE or saliva ejector holders used during a dental procedure on a patient may be unsterile at the beginning of the procedure. In the worst case scenario, the strainer/filter unit, aspirator/HVE, saliva ejector holders, water lines and/or air compressor lines may contain solid, fluids and/or airborne (e.g. vapor) substances from prior patients. This poses a danger that substances and debris from dental procedures performed earlier in the day may cross-contaminate (as by back flowing solid or fluid as well as airborne substances into the patients' mouth or due to the suck-back phenomenon) who is undergoing a dental procedure later on that day. The Center for Disease Control (CDC) in the United States does recommend that all items entering the mouth be sterile but this is not mandated by law. The National Institute of Health (NIH) in the United States has established "Universal Precautions" and guidelines to prevent this type of cross-contamination. Therefore, if a dentist is motivated to use a sterile strainer/filter unit for each patient, the dentist must make a considerable investment in strainer/filter units and must incur increased operating expenses to clean and sterilize them. Secondly, existing strainer/filter units are not versatile (the saliva ejector shown in U.S. Pat. No. 3,890,712 by Lopez is an example of such a non-versatile device). Prior art strainer/filter units are designed to work only with a particular type of saliva ejector or aspirator and cannot easily be used with other types of similar devices. Thirdly, existing sterile strainer/filter units are relatively expensive. The Osseous Coagulum Trap being sold through Quality Aspirators of Duncanville, Tex., is an example of an expensive strainer/filter unit. Fourthly, the cost and time associated with emptying and replacing dental unit traps can be high. Lastly, existing strainer/filter units do not properly filter all amalgam particles (whether in solid, liquid or vapor form) and keep the amalgam from regurgitating. Due to the pore size of existing strainer/filter units, small particles of amalgam waste enter the dental units or cuspidors and water waste lines resulting in amalgam particles (solid, liquid or vapor form) accumulating within the dental unit and the suction lines and pump. Some amalgam particles in solid, liquid or vapor form never reach the conventional amalgam separators. Other existing strainer/filter units with some or all of the disadvantages discussed above are disclosed in U.S. Pat. Nos. 4,058,896, 4,265,621, 4,464,254, 5,078,603, 5,630,939, 5,779,649, 5,741,134, 5,922,614, 6,428,316, and 7,214,059 and U.S. Patent Application Publication No. 2004/0115590.

Applicant's prior patent, U.S. Pat. No. 6,183,254, discloses a strainer/filter unit that overcomes some of the disadvantages mentioned above by providing a device that can be attached to the aspirator holder or saliva ejector valve. The strainer/filter unit comprises a plastic frustum-shaped strainer within a housing that is capped. The plastic strainer disclosed has multiple openings for filtering. Additionally, this prior art device does not prevent regurgitation or back flow of the amalgam as well as other solids, fluids and airborne gaseous substances collected in the strainer/filter unit.

Therefore, there is a need for an improved disposable single use strainer/filter unit that will overcome these disadvantages and act as an amalgam solid, liquid and vapor collector at the source. The present invention is an improvement of Applicant's prior patent and existing prior art by providing an anti-retraction valve as well as the filter to be designed for solid, liquid and airborne substances to travel a tortuous path when passing through the strainer/filter unit.

SUMMARY OF THE INVENTION

The present invention provides an efficient and effective strainer/filter unit that collects solid, liquid and gaseous matters at the source for use in connection with a vacuum-operated type aspirating system that aspirates liquids, solids and gases, and prevents the back-flow of solids, liquids and gases.

The strainer/filter unit of the present invention overcomes the deficiencies of existing amalgam separators by collecting all solid debris, including amalgam in solid, liquid or vapor form, at the source. No amalgam solid, liquid or vapor particles enter the HVE or saliva ejector holders as well as the dental units and the filters within the dental units, cuspidor and the pipelines of the suction system and suction pump so as to enter the water waste lines of the sewage system. The strainer/filter unit of the present invention advantageously eliminates the need for dental unit traps, chairside traps, cuspidor traps and traps used in the pipelines of the vacuum/suction system and pump by collecting solid, liquid and gaseous matters at the source.

The strainer/filter unit of the present invention comprises a filter within a housing that is enclosed by a cap. The filter has a certain thickness and depth composed of multiple layers of pores whereby the pores of one layer partially overlaps the pores of subsequent adjacent layers and when a suction force or gravity is applied to the strainer/filter unit the amalgam particles and other debris follow a tortuous path towards the outlet port of the strainer/filter unit. If desired the pores may be of different sizes and shapes so as to perform in a more effective manner in collecting debris of a very small size without significantly affecting the flow rate. Notably, the amalgam solid, liquid and vapor particles are of different sizes and shapes and travel and accelerate at different speeds with the smallest particles moving and accelerating the fastest. These small particles tend to collide and aggregate so as to increase in size, thereby being captured by the multiple layers of overlapping pores within the filter. The amalgam particles entering subsequent adjacent layers of the amalgam collector also travel and accelerate at different speeds throughout the multilayered strainer/filter unit in a tortuous manner.

The filter, in one embodiment, is made of a sintered porous plastic material of a certain thickness and depth (i.e. volume) having a pore size within the range of 0.1-400 $\mu m$. In another embodiment, the filter is made of a non-woven polypropylene/polyethylene felt-like material having a pore size in the range of 0.1-400 $\mu m$. The filter can also be made of plastic foam material with similar pore size range. A combination of different filter may be used in the strainer/filter unit.

The housing is preferably made of a plastic material that may be rigid or semi-rigid. The housing has a generally tubular body with opposite open ends. The filter is located within the housing at one open end, with the cap enclosing the filter within the housing. An anti-retraction (i.e. one way) valve is provided between the filter opening and the cap to prevent the regurgitation, backflow and spillage of solid, liquid and airborne matters from the filter back to the saliva ejector or aspirator into a patient's mouth.

The cap has an extension that can be of various sizes, which is adapted to engage different types of saliva ejector or aspirator. The opposite open, outlet, end of the housing is adapted to engage the valve of an aspirator device. Adaptors of rigid or semi-rigid plastic may be provided for the opposite open end of the housing to engage valves of different saliva aspirator devices such as high volume evacuators or saliva ejectors.

Liquid, solid and gaseous matters from a dental patient's mouth enter the saliva ejector or aspirator to the strainer/filter unit at the cap and passing through the anti-retraction valve into the filter. Solid matters, and amalgam solid, liquid or vapor particles, are collected in the filter enclosed by the cap. Other liquid and gas may pass through the filter and into the valve and suction line of the saliva aspirator device. The multiple layers of pores of the filter allow effective collection of particles without significantly adversely interfering with the flow rate passing through it.

In an alternate embodiment, the filter is located within the housing at one open end, with the cap at the opposite open end of the housing. Solid matters are collected in the housing and in the filter.

In another embodiment, the strainer/filter unit may contain carbon or sulfur like substances to aid in the collection of mercury, amalgam and arsenic.

In another embodiment, the strainer/filter unit (with or without an affixed saliva ejector or aspirator) is packaged in a pouch that may be sterile with openable ends to minimize/prevent cross-contamination among patients using the same saliva aspirator device. The pouch can also be optionally sealed for the disposal of the strainer/filter unit and the affixed saliva ejector or aspirator, which contains amalgam solid, liquid or vapor (i.e. mercury and/or methyl mercury).

In another embodiment, more than one saliva ejector or high-volume evacuator are attached to the strainer/filter unit to provide a greater control of moisture and more effective collection of solid, liquid and gaseous matters from a patient's mouth. This prevents the incidence of forming of an aerosol that might result in a bio film throughout the operatory that may be harmful to the patient and operator and subsequent patients treated in the same operatory.

In another embodiment, the strainer/filter unit and related accessories are embedded or coated with biocides, or include antimicrobial factors, which reduce the incident of hospital/dental acquired infections.

In another embodiment, the strainer/filter unit may be used as a diagnostic tool of certain diseases by including receptacles, indicator strips or test indicator markers for identifying certain diseases from the saliva or blood passing through the strainer/filter unit.

In another embodiment, the strainer/filter unit may be used to prevent contamination of pipes and water lines from the suck back phenomenon, which reduces the incident of hospital/dental acquired infections and at the same time, also function as a water filter.

The present invention also advantageously eliminates the need to maintain a certain pH level of 5-10 for the suction and water waste pipelines of the vacuum/suction system as required with existing amalgam separators because mercury-containing amalgam does not enter the pipelines. In turn, the release of mercury vapors or methyl-mercury at a level dangerous for human exposure is limited because the strainer/filter unit containing the amalgam can be easily disposed of prior to using chemical such as bleach that may adversely affect amalgam, changing it into toxic methyl mercury.

The strainer/filter unit of the present invention can be either disposable for single-use or parts of it sterilizable for multiple uses. The strainer/filter unit of the present invention in one form can capture 95-99% or greater of amalgam solid, liquid and vapor particles, and such amalgam particles as small as four (4) to five (5) microns ($\mu m$), that meets and exceeds the ISO 11143 Standard. While rubber dam is not identified by the American Dental Association in their "Best Management Practice" for amalgam, using a rubber dam in conjunction with the strainer of the present invention during a dental procedure can provide effectively close to 99.9% of amalgam solid, liquid and vapor waste capture rate. Further, the strainer/filter unit can be used to measure the exact amount of amalgam waste being generated and discharged from a dental office, and which amount can be verified by a simple cost effective random testing of the strainer/filter unit.

BRIEF DESCRIPTION OF THE DRAWINGS

Preferred embodiments of the present invention have been chosen for purposes of illustration and description and are shown (not to scale) in the accompanying drawings forming a part of the specification wherein:

FIG. 16 shows an alternate strainer/filter unit of the present invention with a cap adapted to receive an additional saliva ejector or aspirator having its own valve control.

FIGS. 17A and 17B show alternate strainer/filter units of the present invention for use in-line with the suction line.

FIG. 18 shows an alternate in-line strainer/filter unit with a cap adapted to receive an additional saliva ejector or aspirator having its own valve control.

DETAILED DESCRIPTION OF THE PREFERRED EMBODIMENTS

Figure 1A:
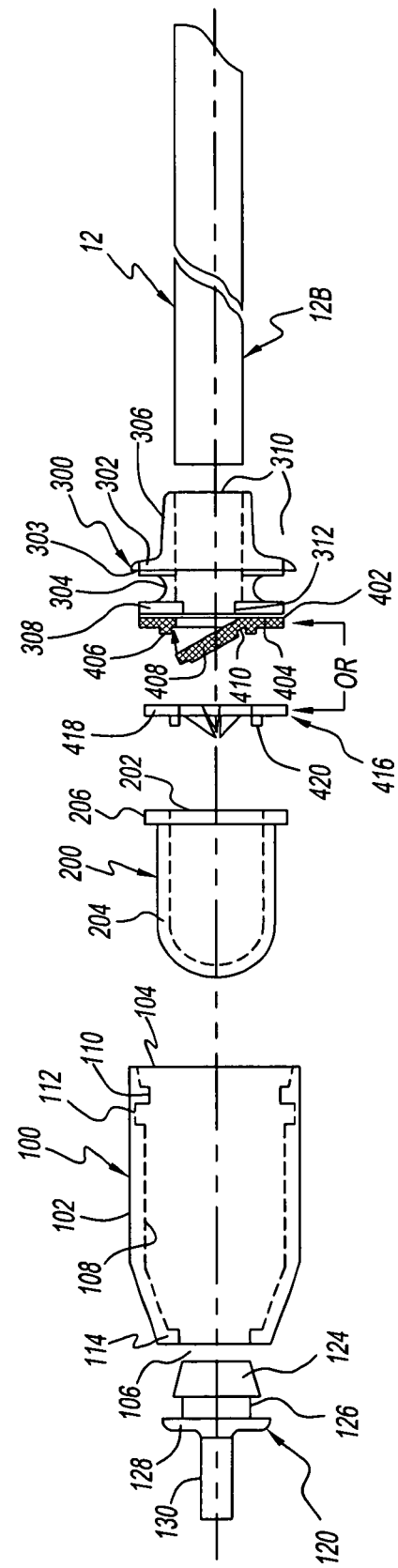
FIG. 1A is an exploded view of a housing, a filter and a cap of the strainer/filter unit of the present invention with an anti-retraction valve.
Figure 2:
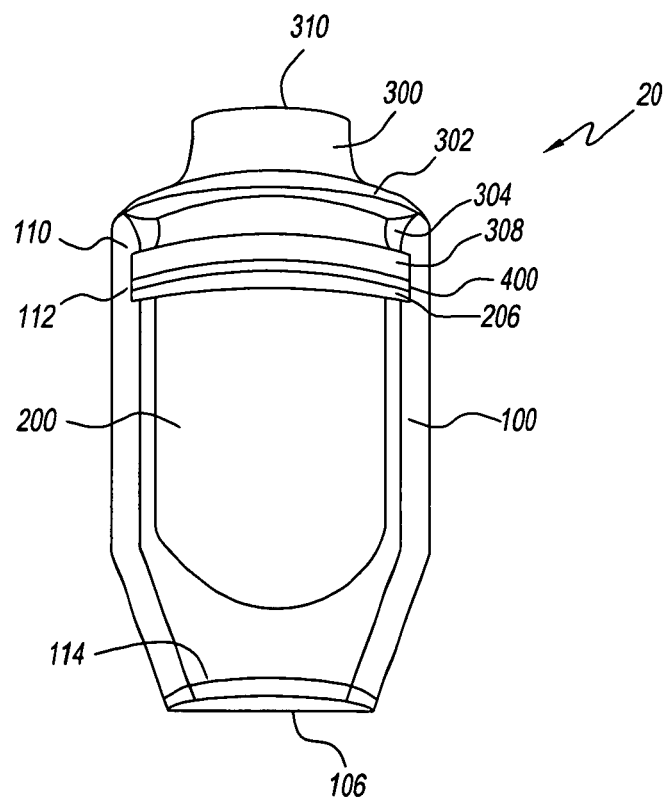
FIG. 2 is an assembled strainer/filter unit of FIG. 1A.

With reference to the drawings wherein the same reference number illustrates the same element throughout, FIGS. 1A and 2 show the strainer/filter unit 20 of the present invention, which include a housing 100, a filter 200 that fits in the housing 100 and a cap 300 that encloses the filter 200 in the housing 100.

As shown in FIG. 1A, housing 100 has a generally tubular body 102 with an inlet end 104 and an outlet end 106. The tubular body 102 is tapered at the outlet end 106. The inner wall 108 of the body 102 at the inlet end 104 tapers to a smaller diameter to form a radially extending lip 110. Abutting the lip 110 is a circular groove 112 with a diameter larger than the inner diameter of the lip 100. The inner wall 108 of the body 102 at the outlet end 106 has a radially extending rib 114 with a diameter smaller than the inner wall 108. The outlet end 106 is adapted to engage the valve of a saliva aspirator device 15 (not shown) or an outlet adaptor 120 before connecting to a saliva aspirator device 15. The rib 114 holds and connects the valve of the saliva aspirator device 15 or the outlet adaptor 120 to the outlet end 106 of the housing 100.

Housing 100 is a unitary piece made of preferably, but not necessarily, a non-rigid and non-opaque material. Housing 100 may be molded. The transparency or translucency of the housing 100 advantageously allows the dentist or dental hygienist to visually inspect the strainer/filter unit 20 to confirm proper operation or functioning and whether capacity is reached. As will be explained in detail later, the non-rigidity of the housing 100 advantageously provides a sealingly snug frictional fit around the filter 200, intermediary anti-retraction valve 400, and cap 300. However, the housing 100 can also be opaque or partially opaque and rigid or partially rigid. The housing can be made from polycarbonate, with or without glass-filled fibers, ABS (acrylonitrile-Butadiene-Styrene) or other plastic-like semi-resilient rubber material.

Filter 200 is a basket 202 with a cylindrical shape and rounded bottom made of a sintered porous plastic material 204 having a certain thickness and depth (i.e. volume). The filter 200 can be molded to form basket 202. At the open end of the basket 202 is a radially extending collar 206 with a diameter larger than the basket 202. The sintered porous plastic material 204 of the basket 202 has adjacent layers of pores or openings that partially overlap each other and are sized and shaped to capture particles smaller than the pore size when matters flow through the material 204 in a torturous path. The sintered porous plastic material 204 allows liquid matters to flow through whereas solid matters are either prevented from passing through the material 204, or are captured within the material 204 as the solid matters attempt to travel through a torturous path within the material 204. Material 204 with different pore sizes can be used for the filter 200 to capture different sized particles. The pore size of the material 204 for a filter 200 may be uniformly sized, but may also be of different sizes. Sealants (such as adhesive) or filler may be added to selective surface or area of the material 204 to allow the filter 200 to capture different sized particles. The sealants or filler may be water-activated such that it becomes tacky for attaching to solid waste or amalgam (in solid, liquid or vapor form) to improve the filtering capability of the filter 200. Adhesive Research, in Pennsylvania, U.S.A., has developed a unique porous adhesive that can be used as the filter 200 without interfering with its performance. The porous adhesive may also enhance the performance of the filter 200 by having pore surfaces that are tacky to which very small particles may adhere to. Also, basket 202 with different thickness and depth of material 204 can affect the flow rate of matters passing through the filter 200. Basket 202 may be molded with the collar 206 as one integral piece. Basket 202 can take on any size and shape, as will be discussed further below. The sintered porous plastic material 204 may be replaced or partially used in combination with a plurality of sheets or layers of plastic foam material, each sheet having at least one aperture or pore that overlaps another aperture or pore of another adjacent sheet or layer. Similarly, the sintered porous plastic material 204 may be replaced or partially used in combination with a non-woven polypropylene/polyethylene felt-like material. The preferred sintered porous plastic material 204 of filter 200 does not significantly adversely affect the flow rate and can capture particles as small as 1/5 to 1/30 of the pore size of the filter 200.

Some examples of material that may be used for filter 200 is disclosed in U.S. Patent Application Publication Nos. 2002/0033365, 2003/0029789, 2003/0211799, 2005/0112397, 2006/0118984, 2007/0062862, and 2007/0256970, and U.S. Pat. Nos. 4,753,728, 5,358,638, 6,030,558, 7,208,222, 7,125,490, and 7,378,020. Consideration of the particle size to be filtered is necessary to select an appropriate material 204 for filter 200. Filter 200 may utilize a combination of surface filtration (which captures particles on the filter's surface) and depth filtration (which captures particles throughout the filter's depth). Generally, four mechanisms cause a particle to be filtered—interception, inertial impaction, diffusion, and electrostatics. Very small particles (<0.01 μm) are typically captured by the diffusion and electrostastics mechanisms, whereas medium sized particles (0.1 to 0.4 μm) are captured by all four mechanisms.

Cap 300 has a disk shape body 302 sized to cover the inlet end 104 of tubular body 102 of housing 100. Cap 300 serves to enclose the filter 200 within housing 100. The disk shape body 302 has an inner extension 304 and an outer extension 306 extending from the inner and outer surfaces of disk shape body 302 respectively. At the perimeter and inner surface of the disk shape body 302 is a step ledge 303. The inner extension 304 is a cylinder having a diameter smaller than the disk shape body 302, with a distal end having an enlarged rim 308 with an outer diameter larger than the cylinder and smaller than the disk shape body 302. The outer extension 306 may have various diameters and lengths adapted to engage different types of saliva ejector or aspirator 12. An opening 310 extends through the cap 300 (i.e. outer extension 306, disk shape body 302, and inner extension 304) to allow matters to flow through the inlet end 104 of tubular body 102 of housing 100 into filter 200. The inner diameter of rim 308 is smaller than the diameter of the through opening 310 to act as an internal stop 312 to prevent a saliva ejector or aspirator 12 inserted into the opening 310 through the outer extension 306 from passing through the cap 300 into the filter 200. Cap 300 can be molded with a hard plastic. Alternatively, cap 300 can be molded in a two-step process such that the disk shape body 302 and inner extension 304 becomes rigid when cured and the outer extension 306 pliable when cured to provide a flexible interaction with a saliva ejector or aspirator 12 inserted into the through opening 310 of the outer extension 306. Further, cap 300 can be made of an opaque or non-opaque material and/or has markers or color coded to indicate the type of saliva ejector/aspirator 12 to be used.

Positioned between the filter 200 and cap 300 is an anti-retraction valve 400. The anti-retraction valve 400 allows solid and liquid matters to travel in one direction only (into the filter 200) and prevents solid and liquid matters from exiting the filter 200 once they enter with the internal stop 312 of cap 300. The anti-retraction valve 400 is made of a resilient material.

FIG. 2 shows the assembled strainer/filter unit 20. Filter 200 is inserted into the tubular body 102 of housing 100 through the inlet end 104. The collar 206 of filter 200 is sized to fit and sit in the circular groove 112 of housing 100 such that the filter 200 cannot be inserted further into the tubular body 102. The rim 308 of cap 300 is also sized to fit and sit in the circular groove 112 of housing 100 abutting the collar 206 of filter 200. The anti-retraction valve 400 is sized to be sandwiched between the collar 206 of the filter 200 and the rim 308 of the cap 300. The collar 206, anti-retraction valve 400 and rim 308 together fits snuggly within circular groove 112. The lip 110 of the tubular body 102 is stretched slightly to allow the insertion of the collar 206 of the filter 200, the anti-retraction valve 400 and the rim 308 of the cap 300 into the circular groove 112 of housing 100. After the collar 206 of the filter 200, the anti-retraction valve 400 and the rim 308 of the cap 300 are inserted into the circular groove 112, the lip 110 rests against the inner extension 304 of cap 300 to provide additional seal. The disk shape body 302 of cap 300 is sized to fit on top of the inlet end 104 of housing 100, with the step ledge 303 resting against the inner wall 108 or lip 10 of tubular body 102 of housing 100. Due to the non-rigidity and resiliency of the housing 100, the interaction among the housing 100, filter 200 and cap 300 is a snug frictional fit to seal the connections. Additionally, adhesives may be employed to further seal the connections. The cap 300 can also be sonically-wielded to the housing 100.

To operate the strainer/filter unit 20, a saliva aspirator or ejector 12 is inserted into opening 310 of cap 300, and the valve of a saliva aspirator device 15 is inserted into the outlet end 106 of housing 100 or into the outlet adaptor 120. Solid and liquid matters withdrawn from a patient's mouth through the saliva aspirator or ejector 12 pass through the strainer/filter unit 20, with liquid matter exiting the strainer/filter unit 20 at the outlet end 106 to the saliva aspirator device 15, and all solid matters are captured in the basket 202 of the filter 200. When a procedure with a patient is completed, the strainer/filter unit 10 is removed from the valve of the saliva aspirator device 15 and either disposed as a whole unit or partially disassembled for disposal (i.e. filter 200) with other parts (i.e. housing 100 and cap 300) of the strainer/filter unit 10 to be sterilized and reused.

Figure 1B:
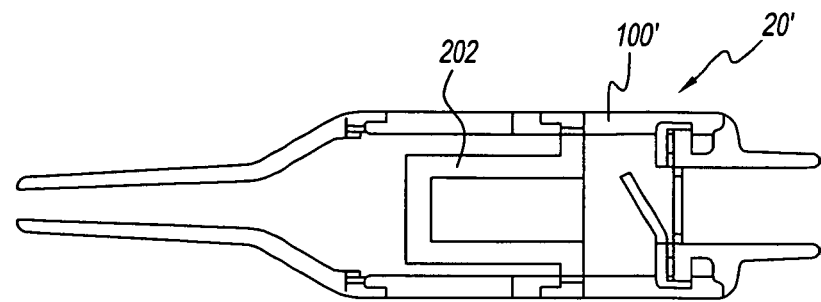
FIG. 1B is an alternate embodiment of the strainer/filter unit of FIG. 1A with larger capacity.

FIG. 1B shows an alternative strainer/filter unit 20' similar to strainer/filter unit 20 of FIG. 1A. Strainer/filter unit 20' has an elongated housing 100' that increases the capacity of the strainer/filter unit 20' and a different shaped filter basket 202.

Figure 3:
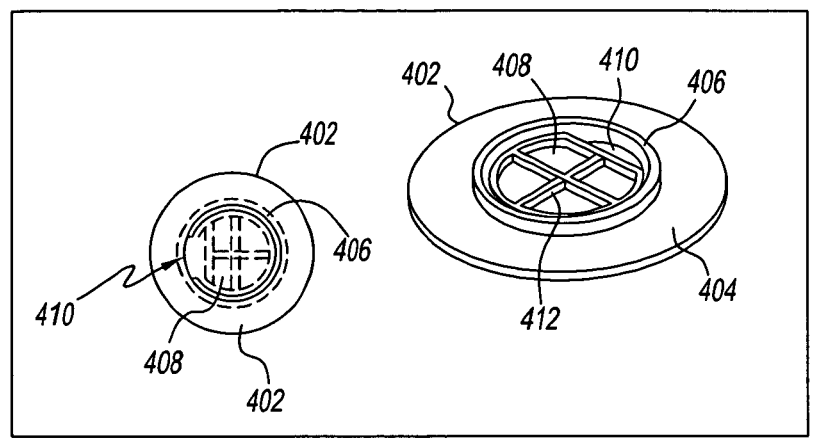
FIG. 3 shows a flapper style anti-retraction valve in a top plan view and a bottom perspective view.

FIG. 3 shows a flapper style anti-retraction valve 402. Valve 402 has a disk shape body 404 with a smaller diameter circular wall 406 extending vertically from one side of the body 404. Within the circular wall 406, the body 404 is partially cut-out to form a flapper 408 that is hingedly connected to the body 404 at 410. The flapper 408 may be reinforced with a pattern of strengthening members 412. The valve 402 may be molded with the flapper 408 hingedly connected to the body 404. The flapper 208 is shown as substantially round, but any other shape can be used.

With the saliva aspirator device 15 in operation and with valve 402 in position as shown in FIGS. 1A and 2, solid and liquid matters pass through the hingedly open flapper 408 to enter the filter 200 of the strainer/filter unit 20. When the saliva aspirator device 15 is turned off, flapper 408 returns to its normal, closed, position (as shown by directional arrow in FIG. 1A).

Figure 4:
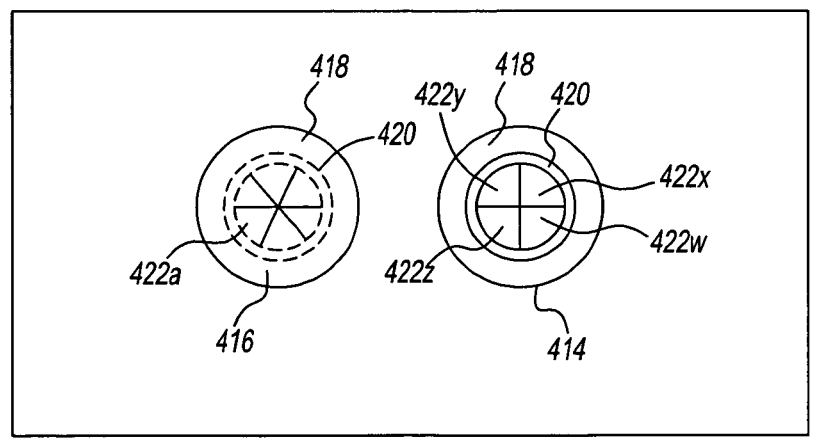
FIG. 4 shows alternate embodiments of the anti-retraction valve with segments, a bottom plan view of one with four segments, and the top plan view of another with six segments.

FIG. 4 shows two alternate segmented, anti-retraction valves 414 and 416. Each valve 414 and 416 has a substantially disk shape body 418 with a smaller diameter circular wall 420 extending vertically from one side of the body 418. Within the circular wall 420, the body 418 is cut along the radial lines to form a plurality of pie-shape segments 422. Valve 414 has four segments 422w-422z and valve 416 has six segments 422a-422d. More or less segments can be used for the anti-retraction valves. While the segments 422 are shown as pie-shape, any other shape can be used. The body 418 within the circular wall 420 is not planar, but forms a cone shape with the point pointing to the same direction as the distal end of the circular wall 420.

With the saliva aspirator device 15 in operation and with valve 414 or 416 in position as shown in FIGS. 1A and 2, solid and liquid matters pass through the spaces between segments 422 to enter the filter 200 of the strainer/filter unit 20. When the saliva aspirator device 15 is turned off, segments 422 returns to its normal, closed, and cone-shape position, which prevents the segments 422 from bending towards in the other direction that may cause solid matters to exit the filter 200.

The anti-retraction valve 400 advantageously retains solid matters within the basket 202 of the filter 200, even when the saliva aspirator device 15 is held and tapped in a downward fashion, without regurgitating of solid (and potentially hazardous) matters. Not only does the internal stop 312 of cap 300 prevents a saliva ejector or aspirator 12 inserted into the opening 310 through the outer extension 306 from passing through the cap 300 into the filter 200, internal stop 312 also prevents the saliva ejector or aspirator 12 from interfering with or distorting the anti-retraction valve 400 that can adversely affect the performance of the anti-retraction valve 400. Without the internal stop 312, a saliva ejector or aspirator 12 may cause the anti-retraction valve 400 to remain partially or fully open, which can result in regurgitation of the solid and liquid matters captured by the basket 202 of the filter 200. The internal stop 312 of cap 300 also advantageously prevents the flapper 408 of valve 402 from opening in the other direction that may cause solid and liquid matters to exit the filter 200.

Figure 5:
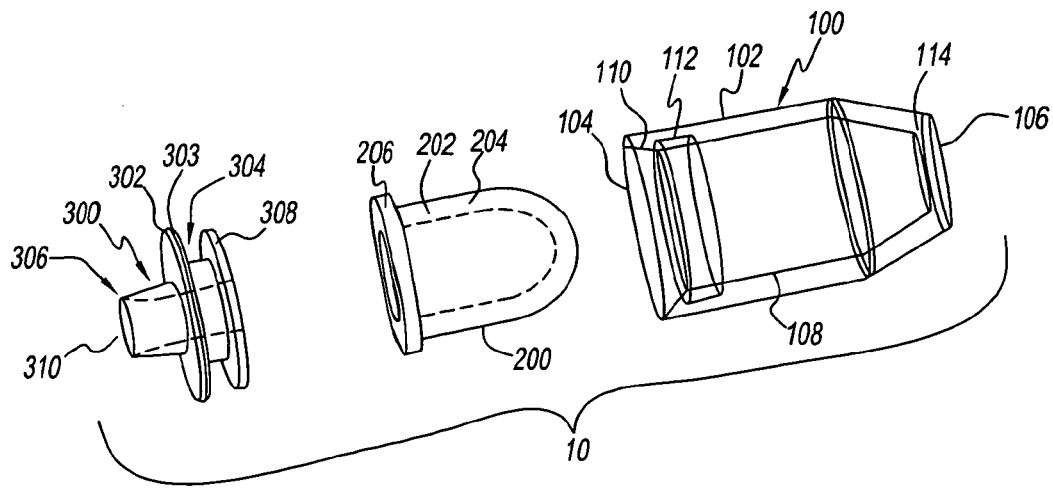
FIG. 5 is an exploded view of another embodiment of the present invention, without the anti-retraction valve.
Figure 6:
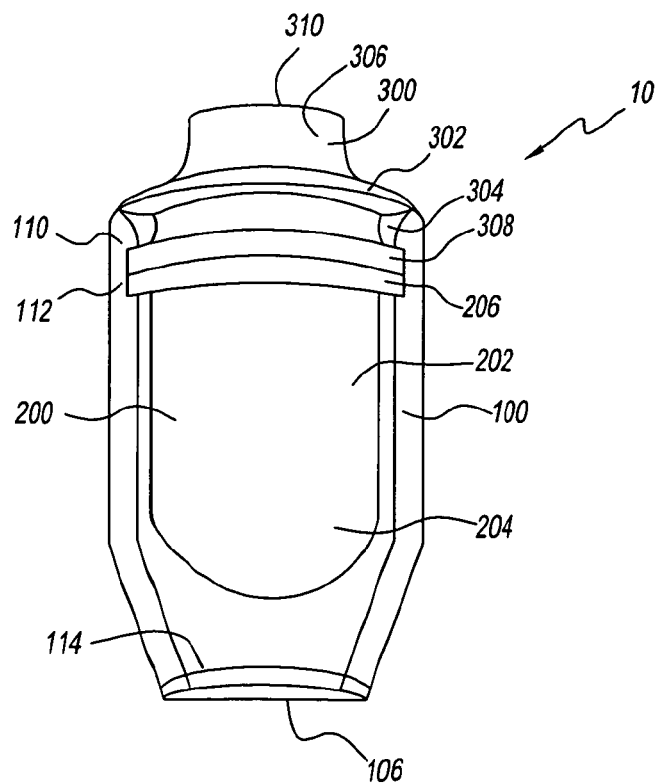
FIG. 6 is an assembled strainer/filter unit of FIG. 5.

FIGS. 5 and 6 show a strainer/filter unit 10 similar to strainer/filter unit 20 of FIGS. 1A and 2 except that it does not have the an anti-retraction valve 400.

Figure 7A:
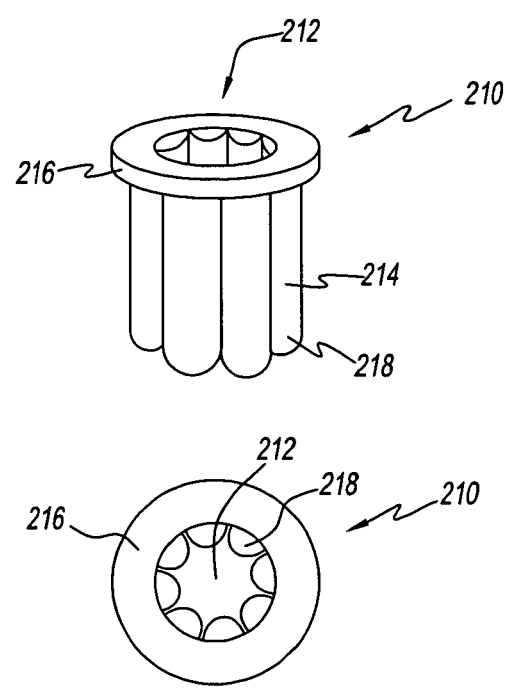
FIGS. 7A-7D show alternate filters of the present invention.
Figure 7B:
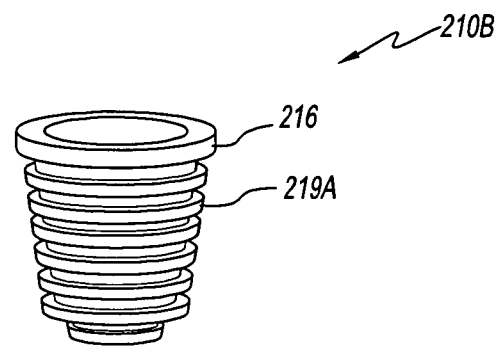
Figure 7C:
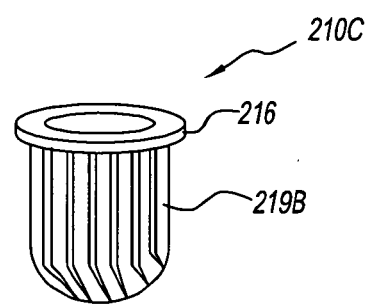
Figure 7D:
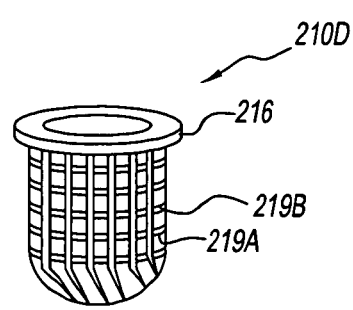

FIG. 7A shows an alternate filter 210A having a basket 212 made of a sintered porous plastic material 214 or non-woven felt material or plastic foam material having a certain depth and thickness, similar to filter 200. At the open end of the basket 212 is a radially extending collar 216 with a diameter larger than the basket 212. Basket 212 has a plurality of vertically and radially, extending ribs 218 on its inner and outer surfaces to provide additional surface areas to improve the flow through the filter 210A. Basket 212 may be molded with the ribs 218 and collar 216 as one integral piece. As illustrated, basket 212 takes on a form different from the basket 202 with a cylindrical shape and rounded bottom of filter 200 of FIG. 1. Any form and shape (e.g. conical, oval, random shape, etc.) basket can be used without detracting from the spirit of the present invention. Other structural extensions or depressions (such as ridges, studs, grooves, channels, etc.) on the basket 212 that can provide additional surface areas can also be used. For example, FIG. 7B shows an alternate filter 210B similar to filter 200, but having a plurality of horizontal grooves 219A; FIG. 7C shows an alternate filter 210C having a plurality of vertical grooves 219B; and FIG. 7D shows an alternate filter 210D having a plurality of horizontal grooves 219A and vertical grooves 219B. The horizontal grooves 219A and vertical grooves 219B may have a V-shape cross-section or another other cross-section shapes.

Figure 8:
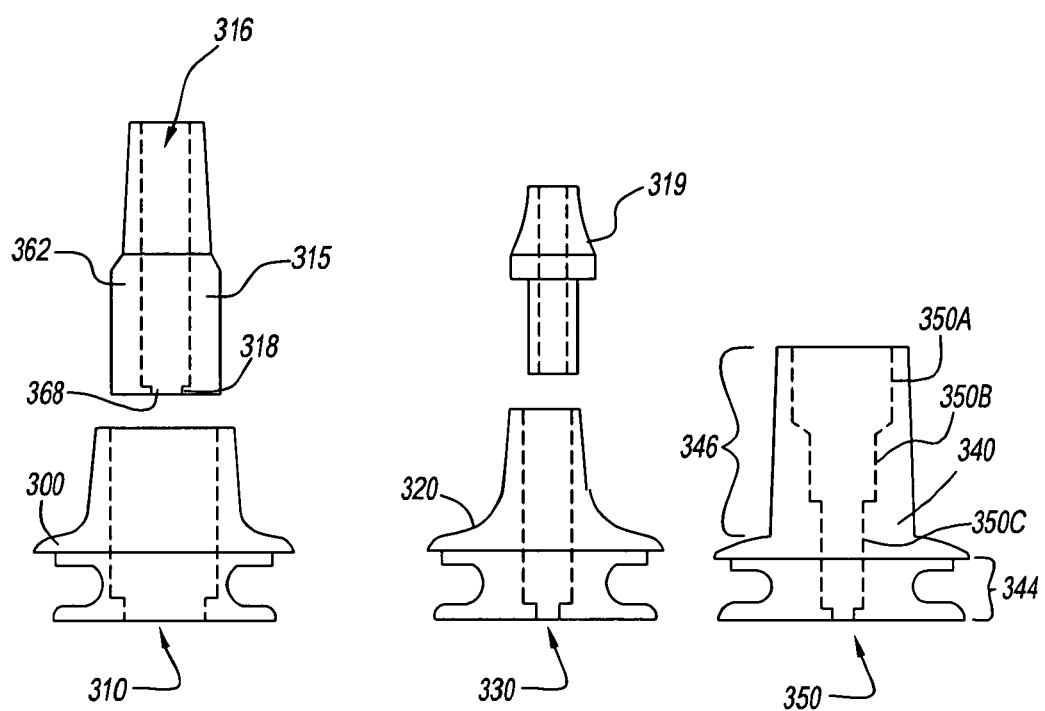
FIG. 8 shows alternate caps and cap adaptors of the present invention.

FIG. 8 shows two alternate caps 320 and 340 and two cap adaptors 315 and 319 for use with the strainer/filter unit 10 or 20 of the present invention. The cap 300, as shown in FIGS. 1-4, has a through opening 310 that is sized to receive a high-volume aspirator/evacuator 12B (see FIG. 3). Cap 320 is identical to cap 300 except that it has through opening 330 that is smaller than through opening 310 of cap 300. Through opening 330 is sized to accommodate any of the other typical saliva ejectors 12A (not shown). Cap 340 is similar to cap 300 and 320 except that it has a through opening 350 that decreases in diameter in a step-wise fashion, from the distal end of the outer extension 346 to the distal end of the inner extension 344. Near the distal end of the outer extension 346 is portion 350A of opening 350 that is sized to receive a high-volume aspirator/evacuator 12B; portion 350B is sized to receive one type of saliva ejector 12A; and portion 350C, near the distal end of the inner extension 344, is sized to receive another, narrower, type of saliva ejector. Cap 340 advantageously can be used with strainer/filter unit 10 or 20 to accommodate all types and sizes of saliva ejector/aspirator 12.

Cap 300 can be converted to cap 330 with the use of a cap adaptor 315. Cap adaptor 315 has a tapered body 362. The wider portion of tapered body 362 is sized to fit into the through opening 310 of cap 300. The cap adaptor 315 has a through opening 316 that is sized to accommodate any of the other typical saliva ejectors 12A (not shown). At the wider portion of tapered body 362, through opening 316 is slightly smaller in diameter than the through opening 316 to act as an internal stop 318 for a saliva ejector 12A inserted into the opening 316. Cap adaptor 319 is similar to cap adaptor 315, and can convert cap 330 to receive saliva ejectors 12A that is smaller in diameter than those receivable in cap 330 without the cap adaptor 319.

Figure 9:
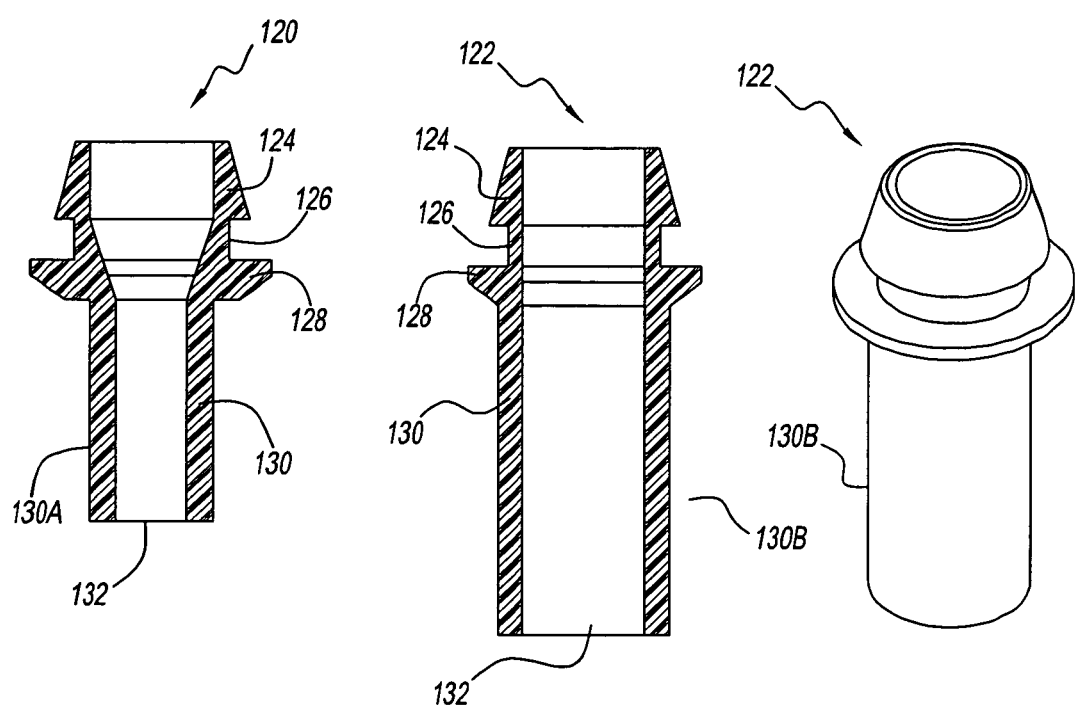
FIG. 9 shows outlet adaptors of the present invention.

FIG. 9 shows two outlet adaptors 120 and 122 for use with housing 100 of strainer/filter unit 10 or 20 of the present invention. As shown in FIG. 1A, outlet adaptor 120 engages the outlet end 106 of housing 100. Each outlet adaptor 120 and 122 has a tapered head 124, a narrower neck portion 126, an enlarged disk 128, and a connecting end 130, with a through opening 132. The tapered head 124 is inserted into the outlet end 106 of housing 100, engaging the rib 114 of housing 100, with the neck portion 126 sized to sealingly abut the rib 114. The enlarged disk 128 is sized to correspond to the tapered end of the tubular body 102. Extending from the enlarged disk 128 is a connecting end 130 sized to be received by the valve of a saliva aspirator device 15. Outlet adaptor 120 has a connecting end 130A sized to be received by the valve of a saliva ejector device (not shown). Outlet adaptor 122 has a connecting end 130B sized to be received by the valve of a high-volume saliva aspirator/evacuator device (not shown). These outlet adaptors 120 and 122 advantageously allow an operator to switch from a saliva ejector device to a high-volume saliva aspirator/evacuator, or vice versa, if one of the devices malfunctions. The outlet adaptors 120 and 122 may be made of a plastic material that may be rigid or semi-rigid.

Figure 10A:
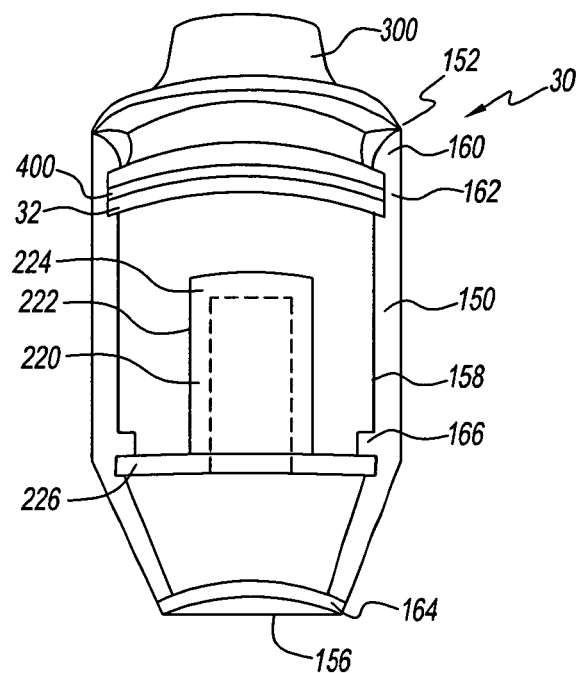
FIGS. 10A and 10B are alternate strainer/filter units of the present invention.

FIG. 10A is another alternative strainer/filter unit 30 of the present invention including a housing 150, a filter 220 that fits in the housing 150 and a cap 300 that encloses the filter 200 in the housing 150. Cap 300 is the same as that described above in connection with strainer/filter unit 10 and 20.

Housing 150 has a generally tubular body 152 with an inlet end 154 and an outlet end 156. Similar to housing 100 of strainer/filter unit 10 and 20, the tubular body 152 is tapered at the outlet end 156. The inner wall 158 of body 152 at the inlet end 154 tapers to a smaller diameter to form a radially extending lip 160. Abutting the lip 160 is a circular groove 162 with a diameter larger than the inner diameter of the lip 160. The inner wall 158 of the body 152 at the outlet end 156 has a radially extending rib 164 with a diameter smaller than the inner wall 158. About midway between the inlet end 154 and outlet end 156 of the tubular body 152, extending from the inner wall 158 is a ring extension 166, which holds and secure filter 220 within the housing 150.

Filter 220 is a basket 222 having a cylindrical shape made of a sintered porous plastic material 224 or non-woven felt material or plastic foam material having a certain depth and thickness. At the open end of the basket 222 is a radially extending collar 226 with a diameter larger than the basket 222 and about the same diameter as the internal wall 158 of body 152. The sintered porous plastic material 224 or non-woven felt material or plastic foam material is the same as that used in the basket 202 of filter 200 described above. Similar to the baskets 202 and 212, basket 222 can take on any form or shape without detracting from the spirit of the present invention.

To form the assembled strainer/filter unit 30 of FIG. 10A, filter 220 is inserted into the tubular body 152 of housing 150 through the inlet end 154. Ring extension 166 stretches to allow the collar 226 of filter 220 to pass through. Collar 226 is then wedged between the ring extension 166 and inner wall 158 of the tapered portion of the tubular body 152. An o-ring 32 that is sized to fit the circular groove 162 is inserted into the circular groove 162. An anti-retraction valve 400 is inserted into the circular groove 162, abutting the o-ring 32. The rim 308 of cap 300 is also sized to fit and sit in the circular groove 162 of housing 150 abutting the anti-retraction valve 400. The o-ring 32, anti-retraction valve 400 and rim 308 together fits snuggly within circular groove 162. In comparison with strainer/filter unit 10 or 20, strainer/filter unit 30 does not collect solid matters in the basket 222 of the filter 200, but instead collects them in the housing 150, between the filter 220 and cap 300, increasing the capacity of the strainer/filter unit 30. To further increase the capacity of the strainer/filter unit 30, housing 150 may be elongated (see strainer/filter unit 30' of FIG. 10B) or enlarged to take on different sizes and shapes.

Figure 11A:
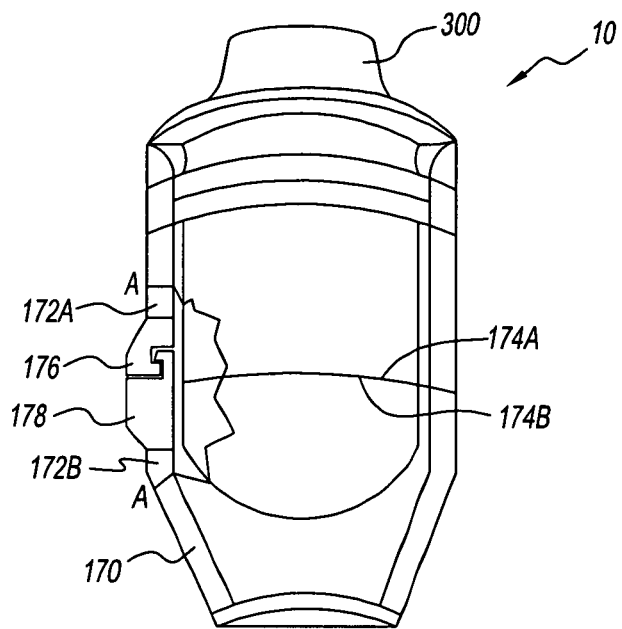
FIGS. 11A and 11B show an alternate housing for the strainer/filter unit of the present invention.
Figure 11B:
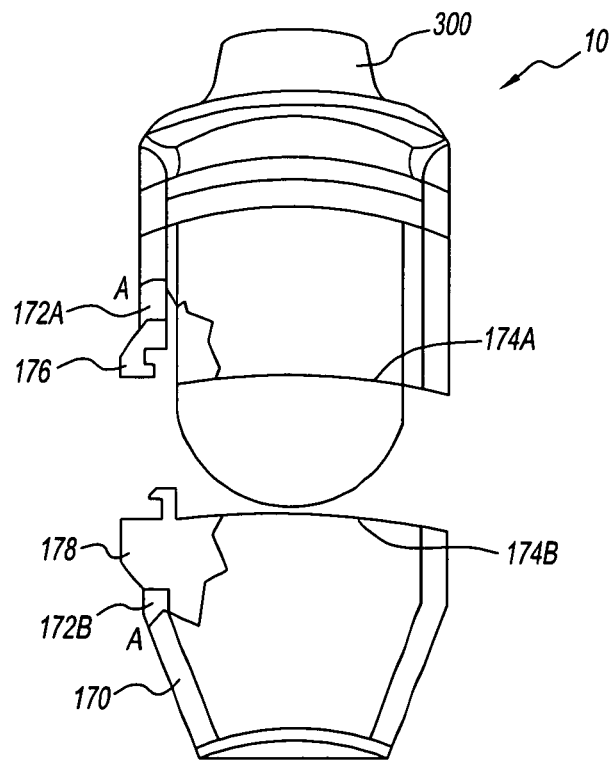

FIGS. 11A and 11B show an alternate housing 170 having a separable tubular body 172 with upper body 172A and lower body 172B. Each of the upper body 172A and lower body 172B has an opposing surface 174A and 174B, respectively, that engages each other. Each opposing surface 174A and 174B may have corresponding tongue and groove to sealing mate with each other. An o-ring (not shown) may be sandwiched between the opposing surfaces 174A and 174B to further seal the interaction between the upper body 172A and the lower body 172B. Upper body 172A has at least one latch element 176 near the opposing surface 174A, and lower body 172B has at least one hook element 178 near the opposing surface 174B. The latch and hook elements 176 and 178 securely hold the upper body 172A and lower body 172B together to form housing 170. The latch and hook elements 176 and 178 may be made of a rigid material, different from the non-rigid material of housing 100, to provide secure holding of the upper body 172A and lower body 172B. The position of the latch and hook elements 176 and 178 can be interchanged such that the latch element 176 is located near the lower body 172B and the hook element 178 is located near the upper body 172A. The latch and hook elements 176 and 178 can also be replaced with other types of fastening components such as tongue and groove; snap fit; protrusion and detent; pressable button and opening; corresponding threading; etc.

The use of housing 170 instead of housing 100 of strainer/filter unit 10 and 20 allows the disposal, after use, of only the upper body 172A and filter 200, while retaining the lower body 172B for sterilization and re-use. For strainer/filter units that collect solid waste in the housing between the filter and cap, such as strainer/filter unit 30 and 30' of FIGS. 10A and 10B, the upper body can similarly be disposed. The upper body 172A to be replaced is provided (or sold) separately to the user so that the user can assemble the strainer/filter unit after sterilization of the other corresponding body.

Figure 12:
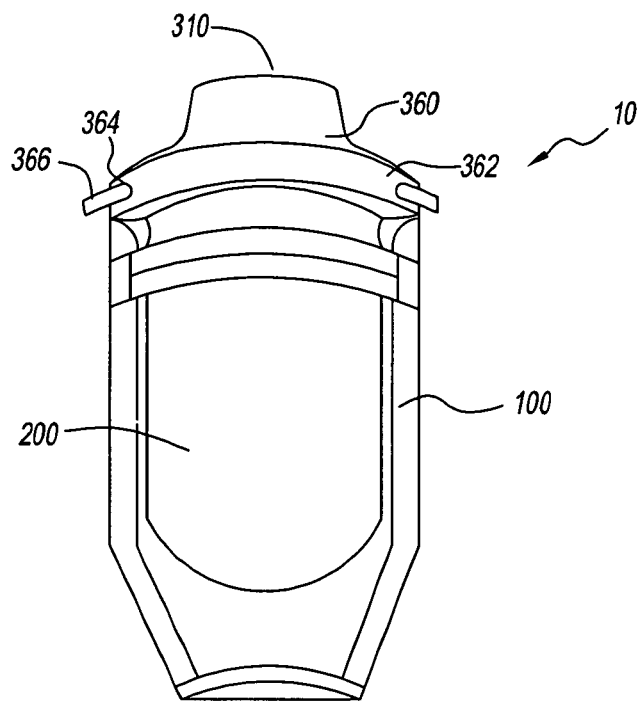
FIG. 12 is an alternate cap with a valve control for the strainer/filter unit of the present invention.
Figure 13:
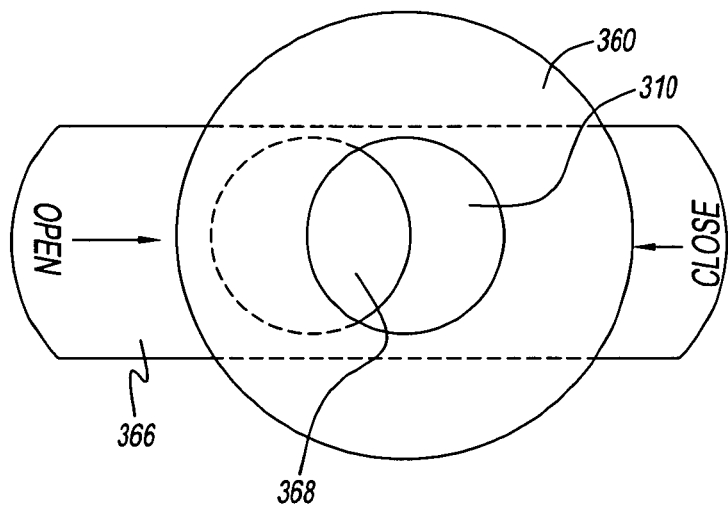
FIG. 13 is a top plan view of the alternate cap of FIG. 12.

FIGS. 12 and 13 show an alternate cap 360 with a valve control for use with a strainer/filter unit 10 of FIG. 6. The valve control of cap 360 replaces the valve control on a saliva aspirator device 15. Cap 360 is similar to cap 300, except that the disk body 362 has a slot opening 364 radially across the disk body 362 that has a width greater than the diameter of the through opening 310. A planar plate 366 is sized to slidably fit into the slot opening 364. Plate 366 has an aperture 368. When plate 366 is pushed in the CLOSE direction (as shown in FIG. 13), the aperture 368 is out of alignment with through opening 310 to close the valve. When plate 366 is pushed in the OPEN direction (as shown in FIG. 13), the aperture 368 is in alignment with through opening 310 to open the valve. Cap 360 advantageously can be connected directly to the vacuum/suction hose of a saliva aspirator device 15 to provide a compact equipment in the dental office that is easier to reach, handle and control. Cap 360 may be made of a material such that it is sterilizable for reuse. Alternatively, cap 360 can be disposed along with the entire strainer/filter unit 10, 20, 20' or 30 after use with each patient. The alternate cap 360 with a valve control can be used with any of the strainer/filter unit 20, 20' or 30 of the present invention.

Figure 14A:
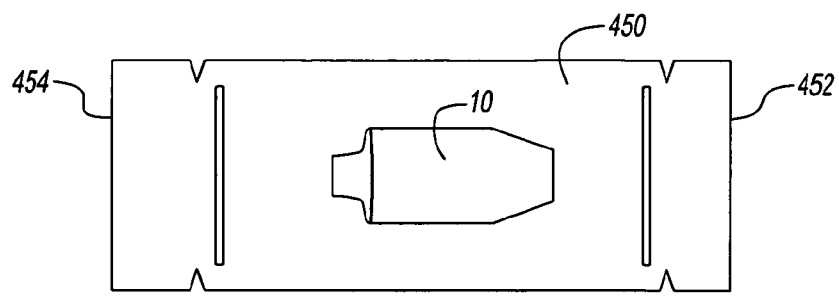
FIGS. 14A-14D show a method of using the strainer/filter unit of the present invention.
Figure 14B:
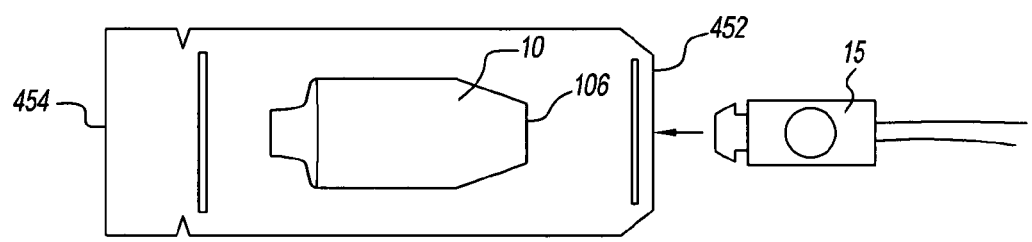
Figure 14C:
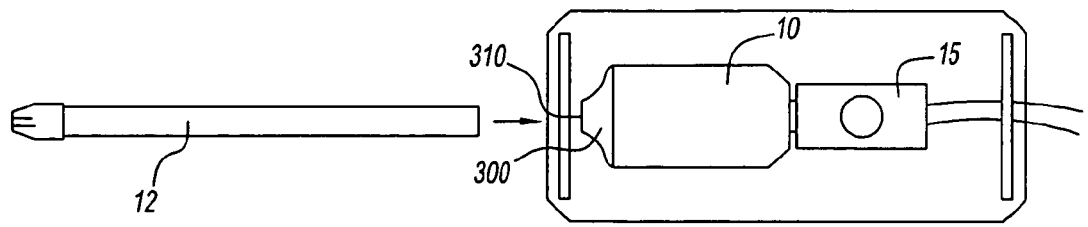
Figure 14D:
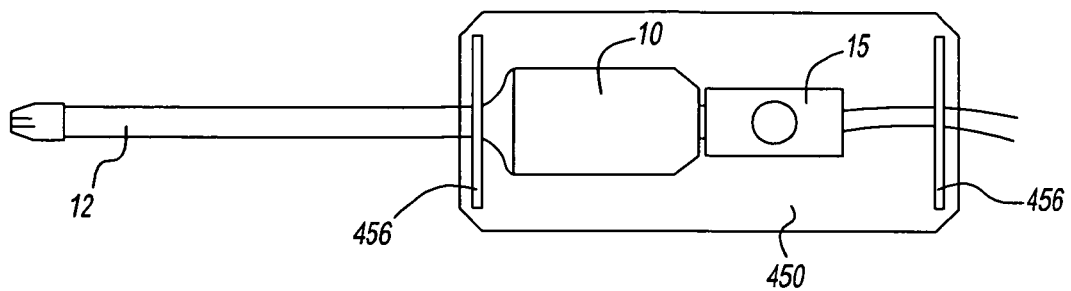
Figure 14E:
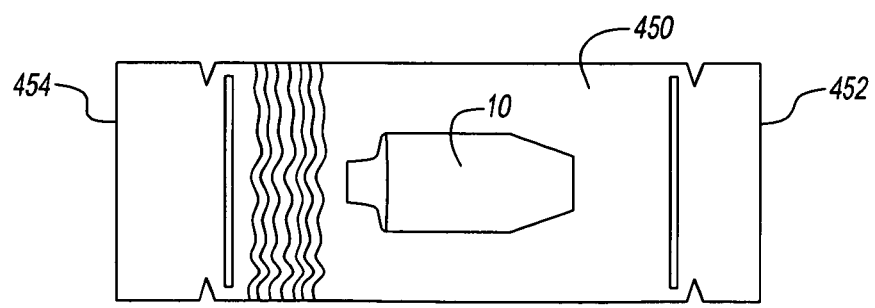
FIG. 14E shows a pouch similar to FIG. 14A, but is expandable.

FIGS. 14A to 14D show the steps of using the strainer/filter unit 10, 20 or 30 of the present invention while maintaining a sterile or aseptic environment. FIG. 14A shows a strainer/filter unit 10 that is packaged and stored in a sterile or clean plastic pouch 450 with opposite ends 452 and 454 that can be opened and re-sealed. One end 452 of the pouch 450 is first opened such that a saliva aspirator device 15 can be attached to the outlet end 106 of strainer/filter unit 10 (FIG. 14B). Next, the other end 454 of the pouch 450 is opened such that a saliva ejector or aspirator 12 can be inserted into the through opening 310 of cap 300 (FIG. 14C). Once both attachments are made, the pouch 450 can be slid over the strainer/filter unit 10 and/or the control of the saliva aspirator device 15 during operation to maintain the sterility of the devices. This also helps to minimize or prevent cross-contamination among patients using the same saliva aspirator device 15. When the procedure is completed, the saliva aspirator device 15 and the saliva ejector or aspirator 12 can be disconnected from the strainer/filter unit 10. The strainer/filter unit 10 with solid waste collected within it can be safely discarded as hazardous waste by first resealing the pouch 450 by closing the sealing elements 456 on each end 452 and 454 of pouch 450. Sealing elements 456 can be adhesive elements or tongue and groove combination or other similar elements known to one skilled in the art. While FIGS. 14A to 14D show the pouch 450 containing only the strainer/filter unit 10, pouch 450 can optionally be packaged and sized to include both the strainer/filter unit 10 and an affixed saliva ejector or aspirator 12. In such configuration, the pouch 450 can be resealed to dispose of both the strainer/filter unit 10 and the affixed saliva ejector or aspirator 12. Further, as shown in FIG. 14E, pouch 450 can be expandable (such as with folded sleeves) such that it can be expanded to dispose of both the strainer/filter unit 10 and the saliva ejector or aspirator 12.

Figure 15:
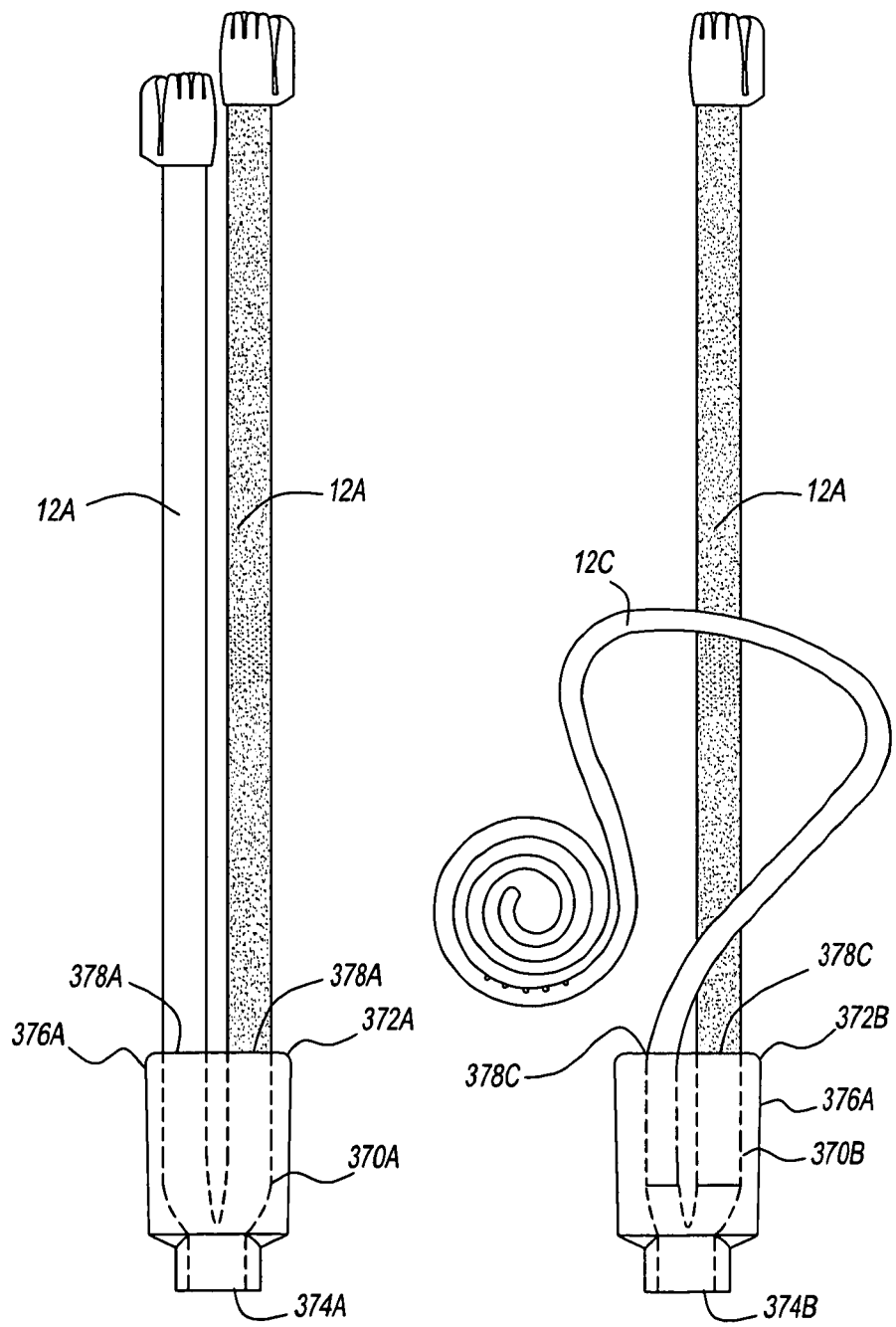
FIG. 15 shows double saliva ejector or aspirator cap adaptors of the present invention.

FIG. 15 shows two types of double cap adaptor 370 (370A and 370B) that allow two saliva ejectors or aspirators to be connected, simultaneously to a strainer/filter unit 10, 20 or 30 or to a valve of a saliva aspirator device 15. This advantageously provides greater control of moisture in and effective collection of solid and liquid matters from a patient's mouth. Thereby, prevents the forming of an aerosol that might result in a bio film throughout the operatory that may be harmful to the patient and operator. Each double cap adaptor 370 has an inlet end 372 and an outlet end 374. The outlet end 374 is shaped and sized to fit in through opening 310 of cap 300 or directly to a valve of a saliva aspirator device 15. The inlet end 372 has an enlarged head 376 to accommodate two openings 378. The openings 378 are sized to accommodate different saliva ejector/aspirator 12. The two openings 378 extend from the inlet end 372 to the outlet end 374 and are merged together towards the outlet end 374. As illustrated in FIG. 15, double cap adaptor 370A receives two identical saliva ejectors 12A; whereas double cap adaptor 370B receives two different types of saliva ejectors 12A and 12C. Double cap adaptor 370 can have different combination of openings 378 to accommodate different types and sizes of saliva ejectors/aspirators 12. One or both of the openings 378 may also be similar to the step-wise opening 350 of cap adaptor 340 of FIG. 8 to be able to receive a plurality of different sized saliva ejectors/aspirators 12.

FIG. 16 shows an alternate strainer/filter unit 40 of the present invention with a cap 380 capable of receiving an additional saliva ejector or aspirator 12A that has its own valve control 382. Strainer/filter unit 40 is similar to strainer/filter unit 20 of FIG. 1A, except that on the outer extension 384 of cap 380 is an aperture 386 for connecting to an additional saliva ejector or aspirator 12A. Strainer/filter unit 40 advantageously allows selective operation, via valve control 382, of an additional saliva ejector or aspirator 12A attached to the cap 380 at aperture 386 as opposed to a saliva ejector or aspirator (not shown) attached to the through opening 388 of cap 380. In order for the additional saliva ejector or aspirator 12A to function via the aperture 386, an aspirator 12B inserted into the through opening 388 of cap 380 needs to be modified to provide an opening 12C such that aspirator 12B may be rotated within cap 380 so that opening 12C can be optionally positioned in alignment with aperture 386. Cap 380 can be adapted to fit on any of the strainer/filter units discussed above; for example, strainer/filter units 10, 20, 20', 30, and 30'.

Figure 17C:
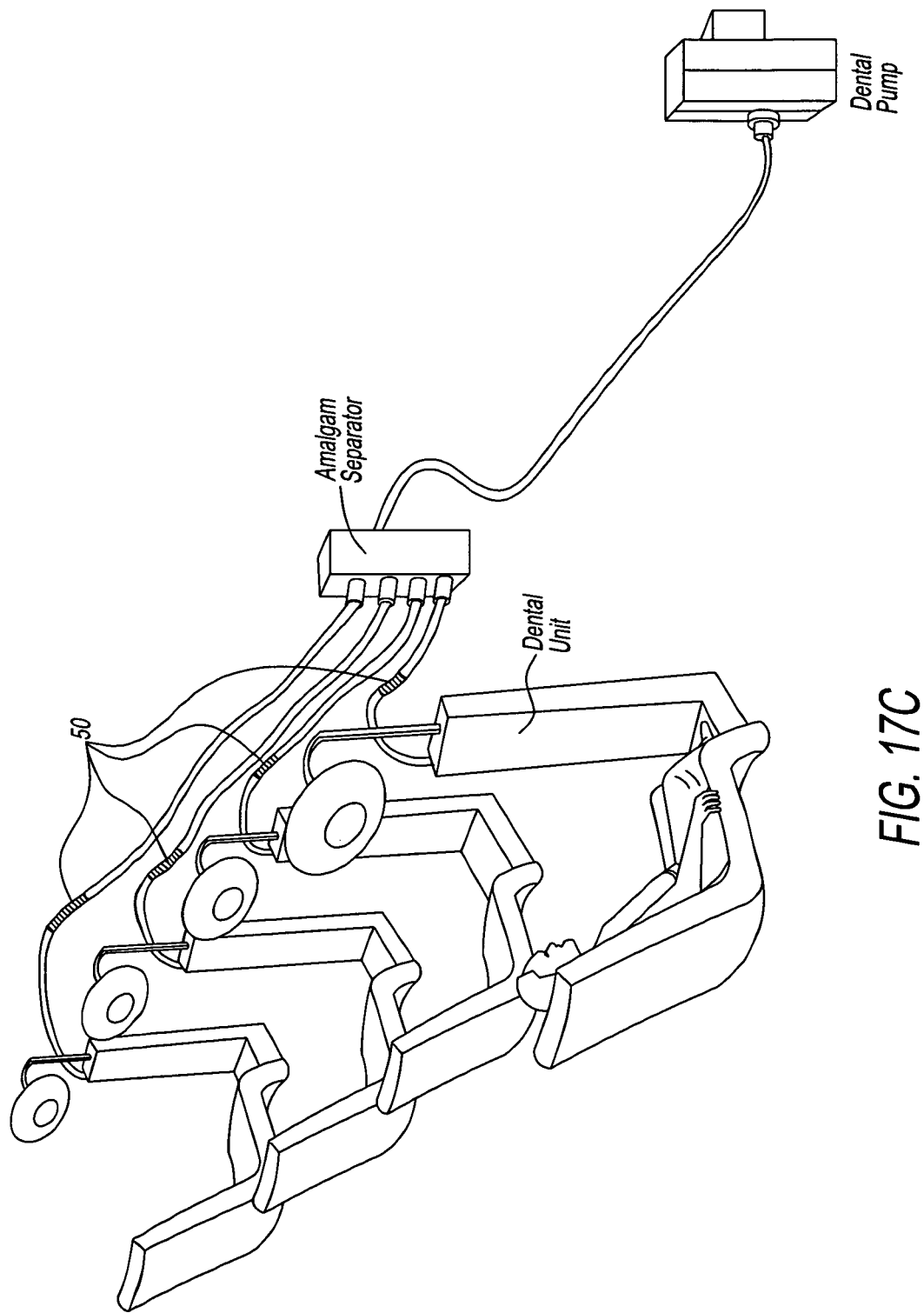
FIG. 17C illustrate the use of in-line strainer/filter units in a dental office.

FIG. 17A shows an alternate strainer/filter unit 50 of the present invention for use in-line with a suction line 14. The previously described strainer/filter units are adapted to be attached to the valve of a saliva aspirator device 15. However, the strainer/filter unit 50 of the present invention can also be located in-line with the suction line 14, not necessarily adjacent the valve of a saliva aspirator device 15. Strainer/filter unit 50 has a generally cylindrical housing 180 that is similarly sized (but not necessarily so) as the suction line 14. A cap 390 similar to cap 300 is positioned at both the inlet end 104' and outlet end 106' of the housing 180. The outer extension 392 of the cap 390 is adapted to frictionally engage suction line 14. It can also be adapted to engage in-line with prior art known methods such as quick release, snap fit, threading, etc. Strainer/filter unit 50 has a filter 200 and flapper valve 402 similar to those described above. FIG. 17B shows a strainer/filter unit similar to 50 of FIG. 17A, but with an elongated housing 180'. FIG. 17C illustrate the use of four in-line strainer/filter unit 50 in a dental office that has four dental chairs and units.

FIG. 18 shows an alternate in-line strainer/filter unit 50' similar to strainer/filter unit 50 of FIG. 17 with a cap 390' similar to cap 390 of FIG. 17 but with an aperture 386 similar to strainer/filter unit 40 of FIG. 16. The aperture 386 connects to an additional saliva ejector or aspirator 12 having its own valve control 382.

Figure 10B:
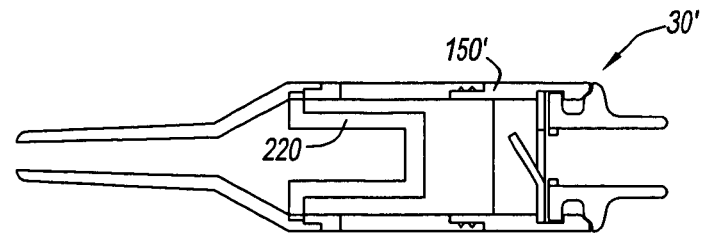
Figure 19:
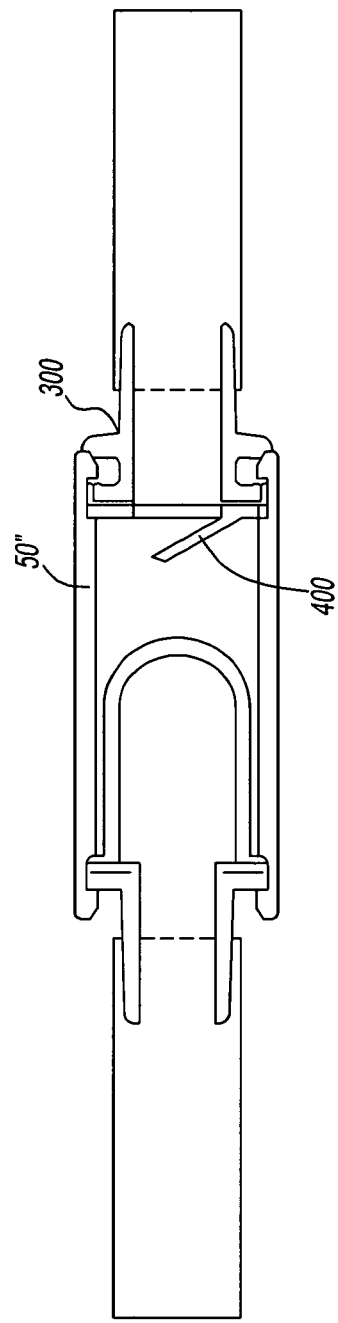
FIG. 19 shows an alternate in-line strainer/filter unit similar to the strainer/filter units in FIGS. 10A, 10B and 17.

FIG. 19 shows an alternate in-line strainer/filter unit 50" similar to strainer/filter units 30, 30' and 50 in FIGS. 10A, 10B and 17, respectively. Similar to strainer/filter units 30 and 30', strainer/filter unit 50" collects solid waste in the housing, between the filter on one end and the anti-retraction valve 400 and cap 300 on the other end, increasing the capacity of the strainer/filter unit 50". The housing is elongated to further increase the capacity.

Figure 20:
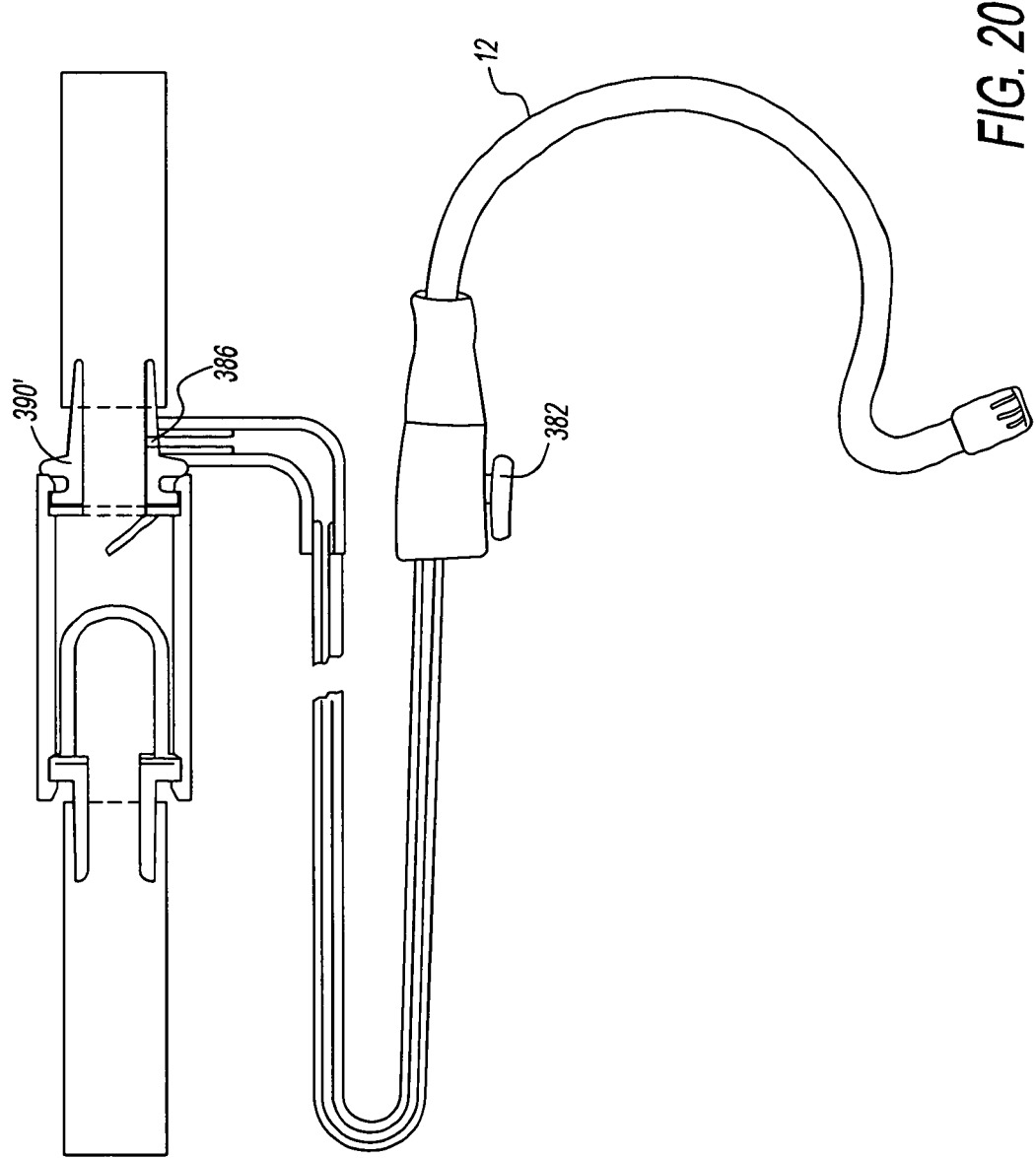
FIG. 20 shows an alternate in-line strainer/filter unit with a cap adapted to receive an additional saliva ejector or aspirator having its own valve control.

FIG. 20 shows an alternate in-line strainer/filter unit similar to strainer/filter unit 50" of FIG. 19 with a cap 390' similar to cap 390 of FIG. 17 but with an aperture 386 similar to strainer/filter unit 40 of FIG. 16. The aperture 386 connects to an additional saliva ejector or aspirator 12 having its own valve control 382.

Figure 21:
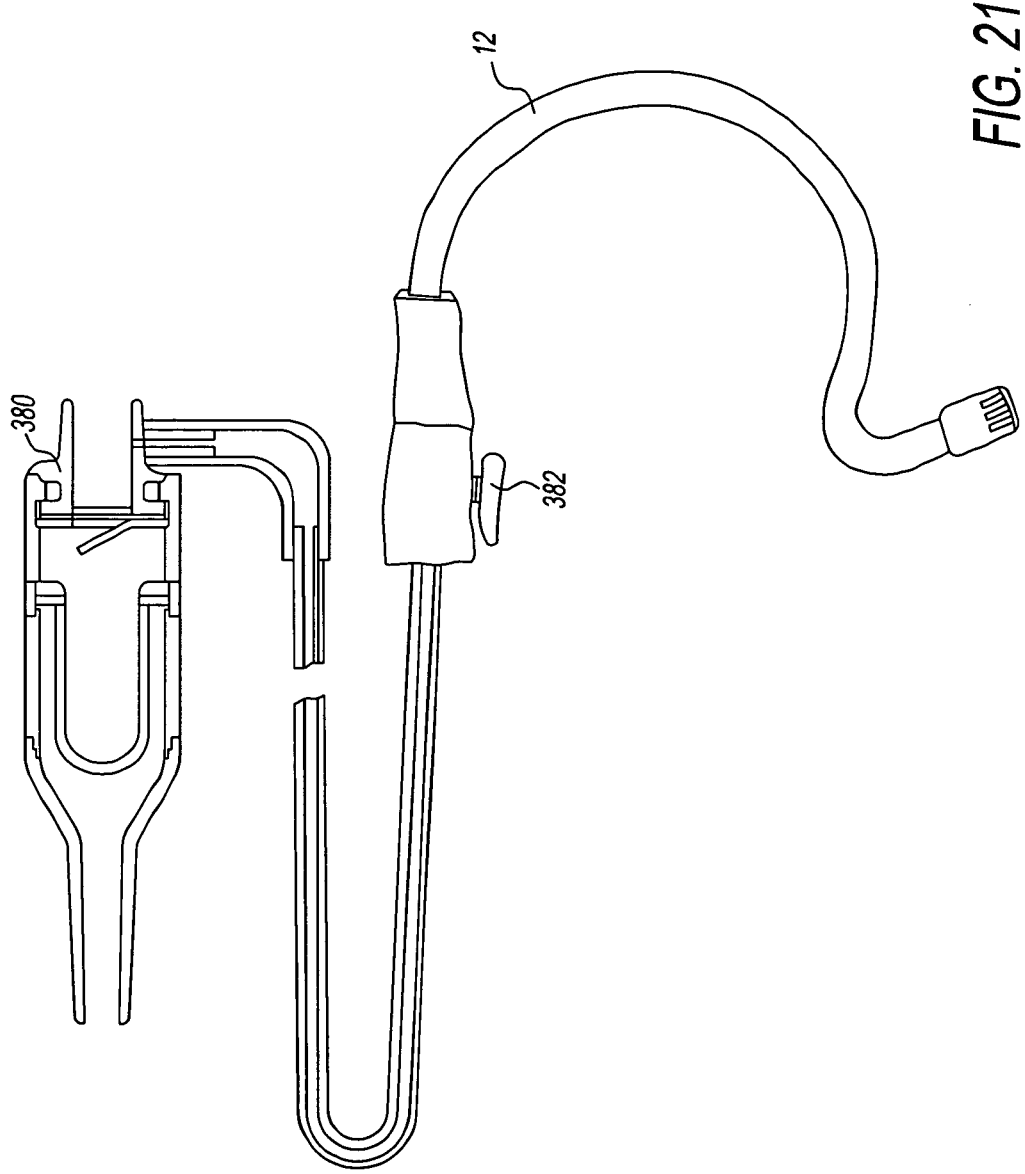
FIG. 21 shows an alternate strainer/filter unit with a cap adapted to receive an additional saliva ejector or aspirator having its own valve control.

FIG. 21 shows an alternate strainer/filter unit similar to strainer/filter unit 40 of FIG. 16, with a cap 380 capable of receiving an additional saliva ejector or aspirator 12 that has its own valve control 382. This strainer/filter unit is similar to strainer/filter unit 40 except that this strainer/filter unit has an elongated housing that increases the capacity to collect solid waste by this strainer/filter unit.

Figure 22:
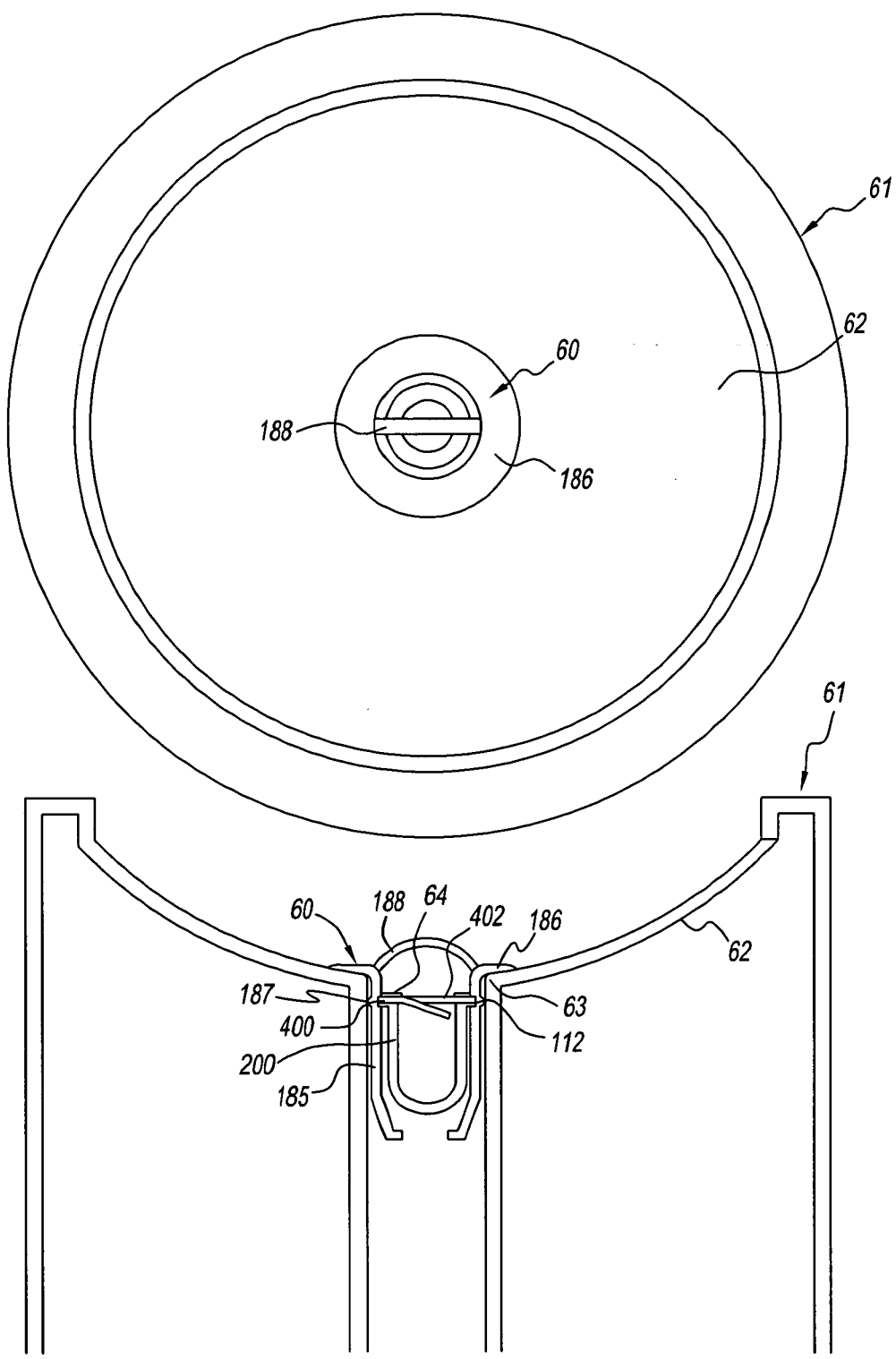
FIG. 22 shows an alternate strainer/filter unit for use in a cuspidor.

FIG. 22 shows the top and cross-sectional views of an alternate strainer/filter unit 60 for use in a cuspidor 61. A typical cuspidor 61 generally is a round basin 62 having a central drain 63. The central drain 63 may or may not be connected to a suction line. Strainer/filter unit 60 has an open-ended tubular housing 185 sized to fit into the central drain 63. The inlet end of housing 185 has an enlarged flange 185 that rests against the basin 62 to prevent the strainer/filter unit 60 from completely falling into the drain 63. On the outer surface of the housing 185 is a seal ring 187 (which may or may not be integral to the housing 185) that engages the inner wall of the drain 63 to provide a seal. A bridge 188 is provided at the inlet end of the housing 185 to facilitate the insertion into and removal of the strainer/filter unit 60 from the drain 63. The inner wall of the housing 185 has a circular groove 112 as in housing 100 described in connection with FIG. 1A. A filter 200 as described in connection with FIG. 1A rests against the circular groove within housing 185. An anti-retraction valve 400, such as a flapper valve 402, covers the opening end of filter 200, and is secured in place with a ring 64 (which can be either permanently or removably).

When solid and liquid matters enter the basin 62 and flow towards the central drain 63 (whether by gravity, venturi effect or affirmative suction), they enter the filter 200 of the strainer/filter unit 60 via the flapper valve 402. Liquid matters pass through the filter 200 and exit the strainer/filter unit 60 into the water waste line. Large solid matters are collected in the basket of the filter 200 and small solid matters travel through pores of the filter 200 through a tortuous path and are collected therein. Upon completion of a procedure or when the strainer/filter unit 60 is filled, it can be easily removed by pulling on the bridge 188 and the entire strainer/filter unit 60 can be safely disposed of as hazardous waste.

Figure 23:
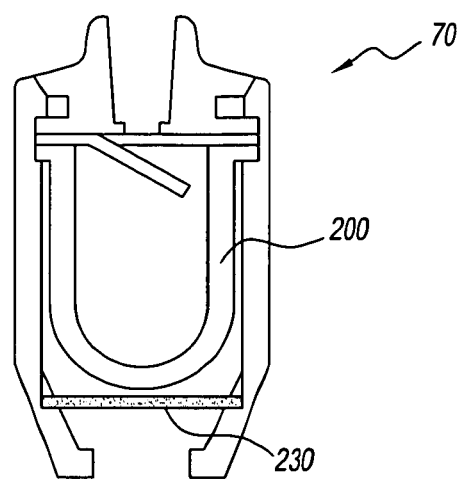
FIG. 23 shows an alternate strainer/filter unit having more than one filter.

FIG. 23 shows an alternate strainer/filter unit 70 having more than one filter. As an illustration, strainer/filter unit 70 is similar to strainer/filter unit 20 of FIG. 1A, except that a secondary filter 230 is provided below filter 200. The secondary filter 230 has a disk shape with certain thickness. The secondary filter 230 can be a plurality of sheets or layers of plastic foam material, with each sheet having at least one pore that overlaps another pore of another adjacent sheet. The secondary filter 230 can also be made of a sintered porous plastic material 204 as filter 200. The secondary filter 230 can also be made of a non-woven polypropylene/polyethylene felt-like material. The secondary filter 230 can also be made of a single sheet of a sieve-type filter. Other material known in the art can be substituted for either filter 200 or secondary filter 230. Filter 200 and secondary filter 230 can have any different combination of materials, shapes, sizes, pore size, filtering capabilities, etc. More than two filters can be used in the strainer/filter unit 70 as necessary or desired. The strainer/filter unit 70 having more than one filter improves the collection of solid matters through the filters.

Figure 24:
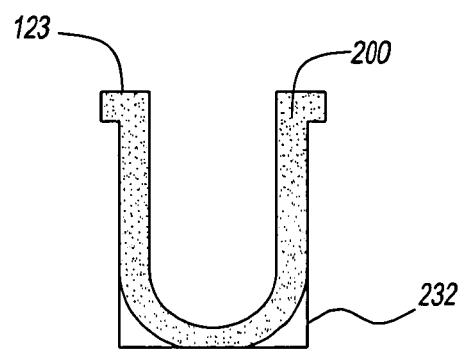
FIG. 24 shows a different combination of two filters for the strainer/filter unit of FIG. 23.

FIG. 24 shows a different combination of filter 200 and a secondary filter 232 that can be used for the strainer/filter unit 70 of FIG. 23. Secondary filter 232 has a basket shape that wraps around the outer surface of filter 200.

Figure 25:
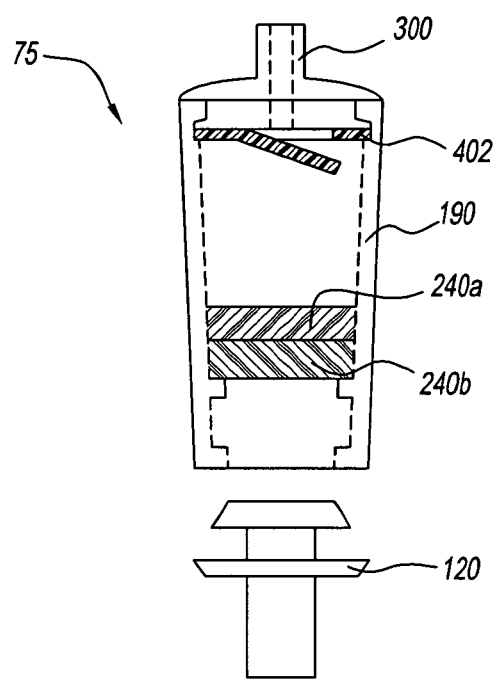
FIG. 25 shows an alternate strainer/filter unit having one or more disk shape filter.

FIG. 25 shows an alternate strainer/filter unit 75 having one or more disk shape filter 240. Strainer/filter unit 75 has a slightly tapered tubular body 190, similar to housing 100 of FIG. 1A. Similar to strainer/filter unit 20 of FIG. 1A, strainer/filter unit 75 has a cap 300 at the inlet end, an outlet adaptor 120 at the outlet end, and an anti-retraction valve 400, such as a flapper valve 402, adjacent the cap 300. Instead of filter 200 having a basket shape for strainer/filter unit 20 of FIG. 1A, strainer/filter unit 75 utilizes one or more disk shape filter 240 positioned in the housing 190. Each disk shape filter 240 is formed from a plurality of layers of material, with each layer having at least one pore that overlaps another pore of another adjacent layer, such that solid matters are collected therein while traveling through it via a tortuous path. Different material can be used for the disk shape filter 240, such as sintered porous plastic material, a non-woven polypropylene/polyethylene felt-like material, and a single sheet of a sieve-type filter. When more than one disk shape filters 240 are used, any different (of same) combination of material and pore sizes can be used. For example, filter 240a can be a 4-5 µm felt material and filter 240b a 100-130 µm sintered porous plastic material.

Figure 26:
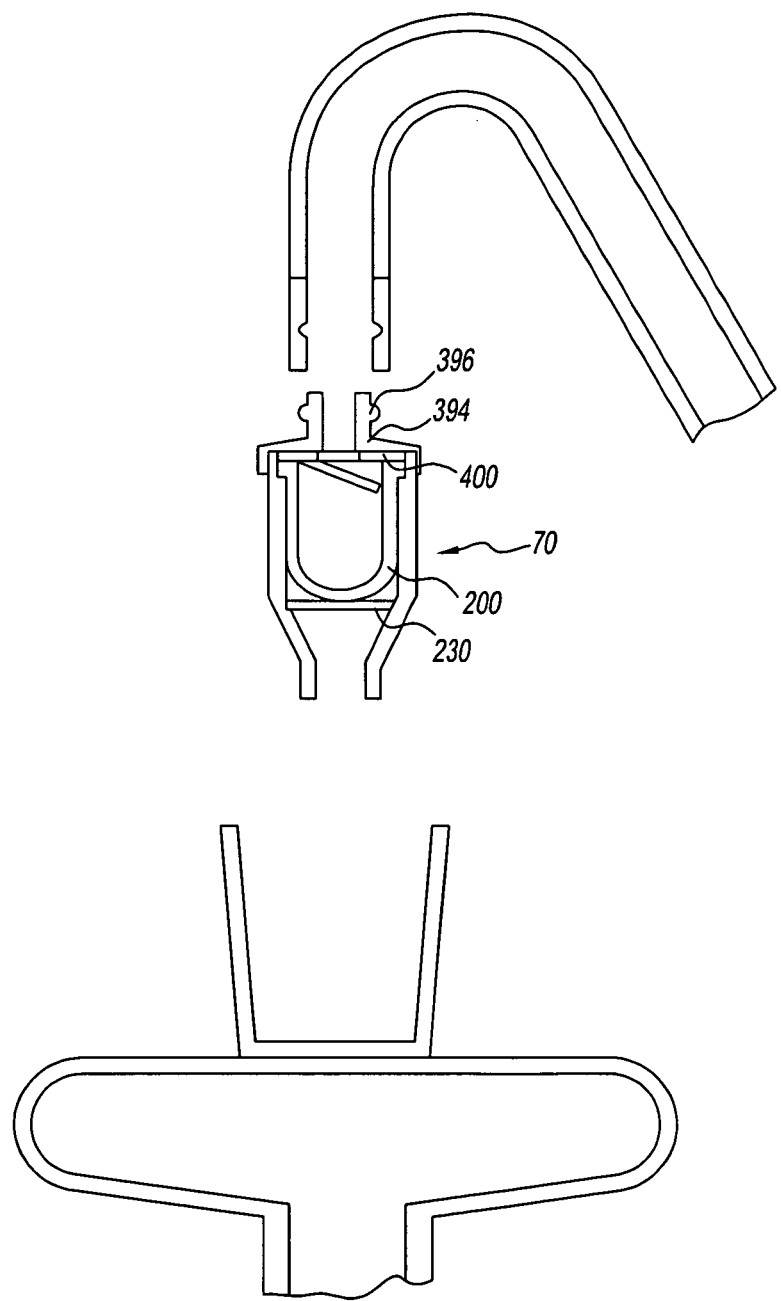
FIG. 26 shows a strainer/filter unit for a dental sink spout that prevents contamination caused by the suck back phenomenon and also acts as a water filter.

FIG. 26 shows a strainer/filter unit 70 for use at a dental sink spout. Any versions of the strainer/filter unit previously described can be used at the dental sink spout provided that cap 394 is modified such that it has at least two extending boss 396 for frictional engagement with corresponding dimples on a collar that can be retrofitted to any existing sink spout. Other methods known to one skill in the art can be used to attach strainer/filter unit 70 to the dental sink spout. When the water is turned on, water passes through the anti-retraction valve 400 and then filter 200 before exiting; thereby filtering any contaminants from the water. When the water is shut off, the suck-back phenomenon is minimized because the anti-retraction valve 400 prevents air from flowing into the sink spout. Such strainer/filter unit 70 can be easily replaced daily, weekly or monthly, as applicable or desired.

Figure 27:
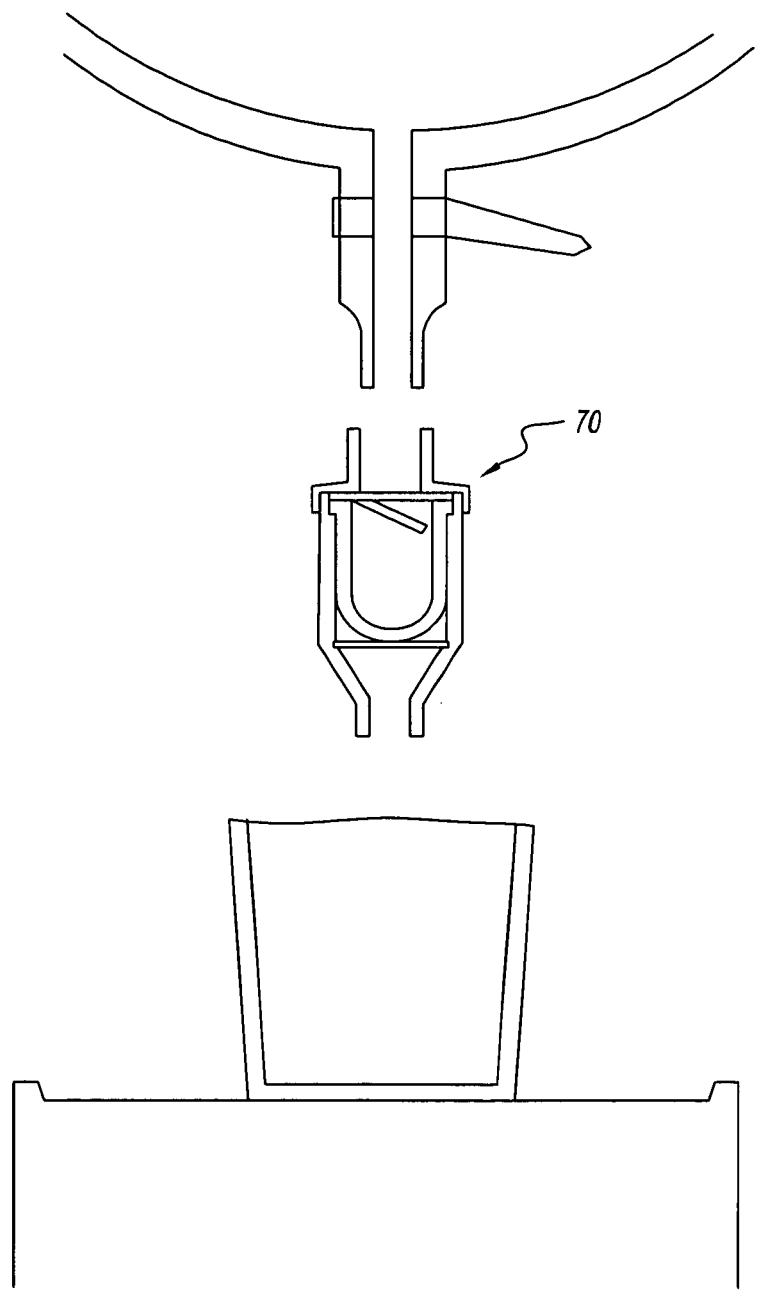
FIG. 27 shows a strainer/filter unit for a water cooler that prevents contamination caused by the suck back phenomenon and also acts as a water filter.

FIG. 27 shows a strainer/filter unit 70 for use at a water cooler having a lever. This strainer/filter unit 70 is shown to be attached to the water cooler outlet by press fitting the cap to the outlet. Other methods known to one skill in the art can be used to attach strainer/filter unit 70 to the water cooler outlet. This strainer/filter unit 70 operates similarly to the strainer/filter unit described in connection with FIG. 26.

Figure 28:
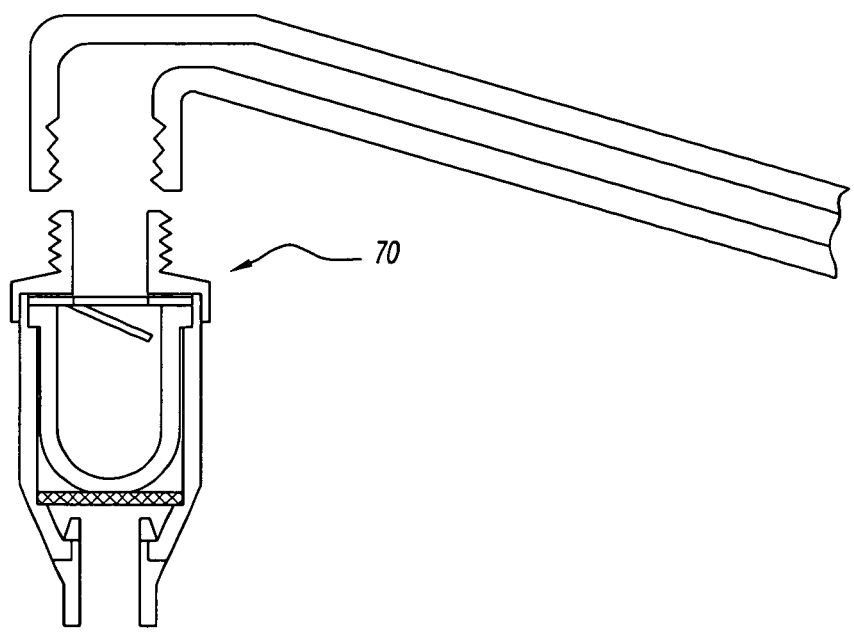
FIG. 28 shows a strainer/filter unit for a sink faucet that prevents contamination caused by the suck back phenomenon and also acts as a water filter.

FIG. 28 shows a strainer/filter unit 70 for use at a sink faucet. This strainer/filter unit 70 is shown to be attached to the sink faucet by threading means. Other methods known to one skill in the art can be used to attach strainer/filter unit 70 to the sink faucet. This strainer/filter unit 70 operates similarly to the strainer/filter unit described in connection with FIG. 26. At the outlet end of the strainer/filter unit 70 is an outlet adaptor similar to those shown in FIG. 9. The outlet adaptor may be replaced more or less frequently than the strainer/filter unit 70. Similar outlet adaptor can be used for the strainer/filter unit shown in FIGS. 26 and 27.

Figure 29:
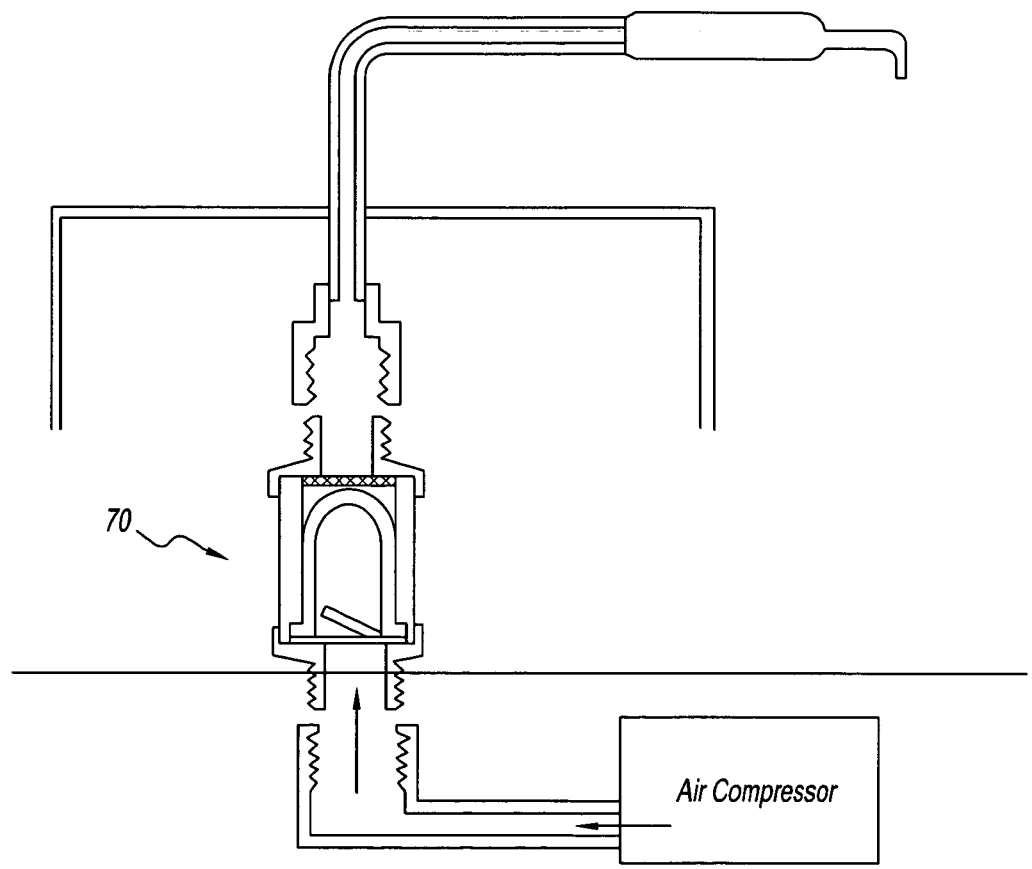
FIG. 29 shows a strainer/filter unit for an air compressor that prevents contamination caused by the suck back phenomenon.

FIG. 29 shows a strainer/filter unit 70 for use with an air compressor that drives a dental hand tool. This strainer/filter unit 70 has threading means at the cap and at the outlet adaptor for attachment to the pipe connecting the hand tool to the air compressor. Other methods known to one skill in the art can be used to attach strainer/filter unit 70 to the pipe. When the air compressor is turned on, water condensation forms in the air compressor and the pipe connected to the hand tool. When the air compressor turns off, the suck-back phenomenon is minimized because the anti-retraction valve 400 prevents the water and air from flowing into the pipes and the air compressor.

The components of the strainer/filter units (e.g. 10, 20 or 30, etc.) of the present invention may be embedded or coated with biocides, or include antimicrobial factors, which can reduce the incident of dental acquired infections. Additionally, other related accessories, such as cap adaptors 315, 319, or 370 and saliva ejectors/aspirators 12 may also be embedded or coated with biocides or include antimicrobial factors.

The strainer/filter units (e.g. 10, 20 or 30, etc.) of the present invention may also be used as a diagnostic tool of certain diseases. The strainer/filter units 10, 20 or 30 may include receptacles, indicator strips or test indicator markers for identifying certain diseases from the saliva or blood passing through the strainer/filter unit 10, 20 or 30.

The strainer/filter units (e.g. 10, 20 or 30, etc.) of the present invention may be coated or embedded with chemicals that show affinity to other harmful chemicals such as lead, mercury, bisphenol, arsenic, zirconium, composites, aluminum oxide, asbestos like material from porcelain and cleaning paste that contains silica, etc. For example, the filter 200, 210A-210D, or 220 or housing 100, 150, or 170 may contain, be coated or embedded with activated charcoal, sulfur compound, iron chelate absorbent, etc. to aid in the collection of these chemicals.

The strainer/filter units (e.g. 10, 20 or 30, etc.) may also contain filters 200, 210A-210D or 220 that can selectively filter certain proteins and DNA fragments.

The strainer/filter units (e.g. 10, 20 or 30, etc.) of the present invention meets the standard set forth for amalgam separators as set forth in New York State's Department of Environmental Conversation's requirements and exceeds the ISO 11143 standard. The strainer/filter unit 10, 20 or 30 collects all solid waste from a patient's mouth to allow precise measurement of the amount of amalgam collected from each patient and from the dental office. Unlike amalgam separators where efficiency of the unit is difficult to test, the strainer/filter unit 10, 20 or 30 can be easily tested with sample amalgam waste.

To those trained in the art, it can be anticipated that different pores size filters may be employed designed to filter out the substances intended. Additionally, it can be anticipated that such filters may be arranged in a specific configuration and the number of filters utilized may vary so as to effectively filter out the substances intended and in most situation, one or more filters may be employed.

Additionally, a purging system for the overall filtering system and its attachments may be employed after each use which may be performed manually or automatically via an activator mechanism so as to flush the filtering system and its adjacent attachments. Thereby further eliminating the effect of the suck-back phenomenon and maintaining the normal performance of said filtering system and its attachment.

Any one of the strainer/filter unit of the present invention may be of a certain enlarged size, having an enlarged filter with an increased surface area so as to be used with more than one aspirator or simultaneously with other aspirators without significantly reducing the flow and ability to capture amalgam solid, liquid and vapor waste according to the present ISO 11143 standard or future governing standard. Furthermore, the strainer/filter unit of the present invention can be enlarged to service multiple dental units and cuspidors and their suction and water waste lines and suction pumps.

The strainer/filter unit of the present invention may be used in conjunction with existing current amalgam separators thereby increasing traditional amalgam separators' efficiency and life span of the unit and filter cartridge. The strainer/filter unit of the present invention may also be arranged in tandem to increase their efficiency and life span. This may even allow the strainer/filter unit to be used at a site approximately 1-6 feet away as an in-line strainer/filter unit thereby servicing several chairs at the same time. Each strainer/filter unit may also be composed of more than one filter or filtering unit so as to be more efficient by increasing the surface area. The secondary and tertiary filters may be assembled in various sizes so as to capture particles of 1 to 5 microns (μm) or greater without significantly affecting the flow rate.

Any one of the strainer/filter unit of the present invention can be used with a rubber dam, which is commonly employed in children and during root canal procedures so as to prevent debris from falling into the patients mouth and possibly being swallowed or aspirated which has been well documented. Rubber dam is a thin elastic like sheet of 4 inches by 4 inches that is perforated with a small hole that goes around a tooth and possibly adjacent teeth when amalgam dental procedures are being performed such as amalgam placement or removal and root canal. The strainer/filter unit of the present invention easily collects amalgam and other debris that has accumulated on the rubber dam a well as the vapor mist and vapor created during procedures involving amalgam (solid, liquid and vapor) thereby protecting the patient as well as the operator during such procedures. Most surprisingly, the ADA has not placed rubber dam on the best practice recommendation list for use when amalgam procedures are being performed.

Any component of the strainer/filter unit of the present invention may be biodegradable so as to be green and friendly to the environment. Further, the strainer/filter unit of the present invention can also be color-coded or numbered to indicate the date or time of use. Additional indicators (such as water actuated color indicators) can be used to remind an operator to change the strainer/filter unit after each use between patients.

To those trained in the art, it can be anticipated that some or all parts of the strainer/filter unit of the present invention may be made of metal, ceramics or other materials.

The features of the invention illustrated and described herein are the preferred embodiments. Therefore, it is understood that the appended claims are intended to cover the variations disclosed and unforeseeable embodiments with insubstantial differences that are within the spirit of the claims.

What I claim is:

1. A portable handheld filter unit for collecting solid matters at a source, the source being liquids, solids, and gases containing said solid matters receivable from a suctioning system having a predetermined flow rate, said portable handheld filter unit comprising:
    at least one aspirator tip having a predetermined diameter;
    a housing having an inlet end and an outlet end, said aspirator tip engages said inlet end, said inlet end receives liquids, solids, and gases containing said solid matters from the suctioning system via said aspirator tip;
    a one-way valve adjacent and at said inlet end of said housing to prevent said liquids, solids, and gases containing said solid matters from exiting said inlet end from said housing;
    a stop between said inlet end of said housing and said valve for both (i) preventing the aspirator tip from contacting said valve to interfere with its operation and (ii) preventing said liquids, solids, and gases containing said solid matters from exiting said inlet end from said housing in cooperation with said valve; and
    at least one disposable depth and thickness filter made of a plurality of abutting layers of sintered porous plastic material having pores of substantially the same fixed pore size greater than 0.1 microns and less than 400 microns with pores from a layer partially overlapping pores of an abutting layer to define a tortuous path through the pores of said filter and having a certain depth and thickness that collects solid matters as small as one fifth to one thirtieth of the pore size within said filter's depth by having said solid matters collide and aggregate while traveling via said tortuous path through the pores of said filter, said filter being positioned entirely within said housing and adjacent said outlet end of said housing;
    wherein the liquids, solids, and gases containing said solid matters entering said inlet end travels through said one-way valve and said at least one filter via said tortuous path through the pores of said filter through the suctioning system with said solid matters as small as one fifth to one thirtieth of the pore size being collected within said at least one filter, with the remaining liquids, solids, and gases exiting said outlet end of said housing immediately without substantially adversely affecting said predetermined flow rate.

2. The portable handheld filter unit of claim 1 wherein said plurality of layers of material comprise different layers of material.

3. The portable handheld filter unit of claim 1 wherein each of said at least one filter is made of a plastic foam material.

4. The portable handheld filter unit of claim 1 wherein said housing having a generally tubular body.

5. The portable handheld filter unit of claim 1 wherein said portable handheld filter unit further comprising a cap at said inlet end of said housing having a through opening for receiving the aspirator tip and enclosing said valve between said cap and said housing.

6. The portable handheld filter unit of claim 5 wherein said cap having a valve control means.

7. The portable handheld filter unit of claim 6 wherein said cap having a disk shape body covering said inlet end of said housing and an outer extension extending from the outer surface of said disk shape body receives said at least one aspirator tip, wherein said valve control means comprises a slot opening radially across said disk shape body, and a planar plate sized to slidably fit into said slot opening, wherein said planar plate having an aperture for placing in and out of alignment with said through opening.

8. The portable handheld filter unit of claim 5 wherein said cap having a disk shape body covering said inlet end of said housing and an outer extension extending from the outer surface of said disk shape body, further comprising an adaptor at said outer extension for receiving at least two aspirators tips.

9. The portable handheld filter unit of claim 5 wherein said cap having a disk shape body covering said inlet end of said housing, an outer extension extending from the outer surface of said disk shape body for receiving a first aspirator tip, wherein said outer extension having an aperture for receiving a second aspirator tip having a control valve.

10. The portable handheld filter unit of claim 5 wherein said cap is molded.

11. The portable handheld filter unit of claim 1 for use with at least one aspirator device having a valve, wherein said outlet end of said housing is adapted to engage the valve of the aspirator device.

12. The portable handheld filter unit of claim 1 wherein one of said at least one filter having a basket shape with the basket opening directed towards said inlet end of said housing.

13. The portable handheld filter unit of claim 12 wherein said basket having means for increasing the surface area of one of said at least one filter.

14. The portable handheld filter unit of claim 13 wherein said surface area increasing means comprises a plurality of rib extensions.

15. The portable handheld filter unit of claim 13 wherein said surface area increasing means comprises a plurality of channels.

16. The portable handheld filter unit of claim 1 wherein one of said at least one filter having a basket shape with the basket opening directed towards said outlet end of said housing.

17. The portable handheld filter unit of claim 1 wherein said portable handheld filter unit further comprising a substance having an affinity to bond to a certain harmful chemical within said unit.

18. The portable handheld filter unit of claim 17 wherein said substance contains carbon.

19. The portable handheld filter unit of claim 1 wherein said portable handheld filter unit further comprising a biocide within said unit.

20. The portable handheld filter unit of claim 1 wherein said portable handheld filter unit further comprising antimicrobial factors within said unit.

21. The portable handheld filter unit of claim 1 wherein said portable handheld filter unit further comprising means for diagnosing the presence of certain disease within said unit.

22. The portable handheld filter unit of claim 21 wherein said diagnosing means comprises an indicator strip.

23. The portable handheld filter unit of claim 1 wherein said one-way valve comprises a disk shape body having a partial cut-out defining a flapper that is hingedly connected to said body.

24. The portable handheld filter unit of claim 1 wherein said one-way valve comprises
a generally disk shape body with a central cone shape portion wherein said cone shape portion is cut along a plurality of radial lines to form a plurality of pie-shape segments.

25. The portable handheld filter unit of claim 1 wherein said portable handheld filter unit further comprising an adhesive material applied on selective area of said at least one filter to capture different sized solid matters.

26. The portable handheld filter unit of claim 1 for use with an aspirator having an aspirator valve, wherein said portable handheld filter unit further comprising an adaptor at said outlet end of said housing adapted to receive said aspirator valve.

27. The portable handheld filter unit of claim 1 wherein said housing comprises an upper body and a lower body removably connected to each other such that said one-way valve and said filter may be disposed and replaced.

28. The portable handheld filter unit of claim 1 comprising first and second filters positioned adjacent each other within said housing.

29. The portable handheld filter unit of claim 28 wherein said first filter having a basket shape and said second filter having a disk shape.

30. The portable handheld filter unit of claim 28 wherein said first and second filters are made of different materials.

31. The portable handheld filter unit of claim 28 wherein said first and second filters each having a disk shape.

32. The portable handheld filter unit of claim 1 wherein said housing and valve are molded.

33. The portable handheld filter unit of claim 1 wherein said unit is made of a biodegradable material.

34. The portable handheld filter unit of claim 1 wherein part of said unit is made of a biodegradable material.

35. The portable handheld filter unit of claim 1 wherein part of said unit is made of metal.

36. The portable handheld filter unit of claim 1 wherein part of said unit is made of ceramics.

37. The portable handheld filter unit of claim 1 wherein said portable handheld filter unit further comprising a marking on said unit to indicate a temporal reference.

38. The portable handheld filter unit of claim 1 wherein said portable handheld filter unit further comprising an indicator to show a user that the unit has been used at least once.

39. The portable handheld filter unit of claim 1 wherein the filter is attached to the housing between the outlet end of the housing and the inlet end of the housing;

and further comprising a cap, which is configured to be removably attached to the housing at the inlet end of the housing, so that the filter is between the outlet end of the housing and the cap;

wherein the cap has a substantially cylindrical rim connected to a substantially cylindrical extension;

wherein the substantially cylindrical rim has an outer diameter;

wherein the substantially cylindrical extension has an outer diameter, wherein the outer diameter of the substantially cylindrical extension is less than the outer diameter of the substantially cylindrical rim; and wherein the cap is removably attached to the housing at the inlet end of the housing by removably attaching the substantially cylindrical rim of the cap inside of the housing, so that at least a majority of the substantially cylindrical extension is outside of the housing.

40. The portable handheld filter unit of claim 39
wherein the substantially cylindrical extension has a first inner diameter; and
wherein the substantially cylindrical rim has an inner diameter which is less than the first inner diameter of the substantially cylindrical extension, such that a tube having an outer diameter less than the first inner diameter of the substantially cylindrical extension but greater than the inner diameter of the substantially cylindrical rim, is stopped from moving into the substantially cylindrical rim after being inserted into the substantially cylindrical extension.

41. The portable handheld filter unit of claim 40
wherein the substantially cylindrical extension has a second inner diameter which is larger than the first inner diameter of the substantially cylindrical extension such that a second tube having an outer diameter greater than the first inner diameter of the substantially cylindrical extension but less than the second inner diameter of the substantially cylindrical extension, can pass through into and through a part of the substantially cylindrical extension having the second inner diameter but not through a part of the substantially cylindrical extension having the first inner diameter.

42. The portable handheld filter unit of claim 39
wherein the cap has a disk shaped body located between the substantially cylindrical rim and at least a portion of the substantially cylindrical extension; and
wherein the disk shaped body has an outer diameter greater than an inner diameter of the inlet end of the housing, so that at least a portion of the disk shaped body is configured to abut the inlet end of the housing and sit outside of the housing when the substantially cylindrical rim is removably attached inside of the housing.

43. The portable handheld filter unit of claim 39 wherein the one-way valve is attached inside of the housing between the filter and the cap when the cap is removably attached to the housing at the inlet end of the housing.

44. The portable handheld filter unit of claim 39
wherein the cap is molded in a manner, such that the substantially cylindrical rim is rigid and the substantially cylindrical extension is pliable.

45. The portable handheld filter unit of claim 1 further comprising
a pouch having an inner chamber, a first resealable end, and a second resealable end opposing the first resealable end, wherein the inner chamber is between the first resealable end and the second resealable end;

wherein when the first sealable end and the second resealable end are both completely sealed, the inner chamber is completely sealed;

wherein the first resealable end and the second resealable end can be unsealed to unseal the inner chamber;

wherein after being unsealed, the first resealable end and the second resealable end are configured to be resealable to completely reseal the inner chamber; and wherein the housing, and the filter are located in the inner chamber of the pouch.

46. The portable handheld filter unit of claim 45 wherein
the first resealable end has a length which is greater than a diameter of the inlet end of the housing; and
the second resealable end has a length which is greater than the diameter of the outlet end of the housing.

47. The portable handheld filter unit of claim 45 wherein the pouch is expandable so that a distance between the first resealable end and the second resealable end can be increased.

48. The portable handheld filter unit of claim 45 wherein
wherein the one-way valve is attached inside of the housing between the filter and the inlet end of the housing.

49. The portable handheld filter unit of claim 1 wherein the filter is a molded integral piece having a porous sintered plastic material comprised of at least a first layer and a second layer, wherein the first layer has at least one pore and the second layer has at least one pore, and the at least one pore of the first layer partially overlaps the at least one pore of the second layer.

50. The portable handheld filter unit of claim 1 wherein the housing has first and second portions;
wherein the first and second portions of the housing are in line with each other, substantially parallel to a side of the filter, and each of the first and second portions of the housing overlap at least part of the side of the filter, when the portable handheld filter unit is in an assembled state; and
wherein the first and second portions of the housing are configured to be detached from each other to put the filter into a disassembled state, so that the first portion of the housing remains attached to the filter, but the second portion of the housing is detached from the filter, and the second portion of the housing does not overlap the side of the filter, in the disassembled state.

51. A method of collecting solid matters at a source, the source being solids, liquids, and gases containing solid matters, receivable from a suctioning system having a predetermined flow rate, comprising the steps of:
providing a portable handheld filter unit having at least one aspirator tip with a predetermined diameter, a housing with an inlet end and an outlet end with the aspirator tip engaging the inlet end, a one-way valve adjacent and at said inlet end of said housing to prevent solids, liquids, and gases containing said solid matters from exiting the inlet end from the housing, a stop between said inlet end of said housing and said valve for both (i) preventing the aspirator tip from contacting said valve to interfere with its operation and (ii) preventing said solids, liquids, and gases containing said solid matters from exiting said inlet end from said housing in cooperation with said valve, and at least one disposable depth and thickness filter made of a plurality of abutting layers of sintered porous plastic material having pores of substantially the same fixed pore size greater than 0.1 microns and less than 400 microns with pores from a layer partially overlapping pores of an abutting layer to define a tortuous path through the pores of said filter and having a certain depth and thickness that collects solid matters as small as one fifth to one thirtieth of the pore size within the filter's depth by having said solid matters collide and aggregate while traveling via said tortuous path through the pores of the filter, the filter being positioned entirely within said housing and adjacent said outlet end of said housing;

providing suctioning force at said outlet end of said housing; and extracting said solid matters by having the solids, liquids, and gases containing said solid matters enter said housing via the inlet end, passes through said one-way valve and travels through the at least one filter via said tortuous path through the pores of the filter through the suctioning system with solid matters as small as one fifth to one thirtieth of the pore size being collected within said at least one filter, with the remaining solids, liquids, and gases exiting the outlet end of the housing immediately without substantially adversely affecting the predetermined flow rate.

52. The method of claim 51 providing first and second filters, wherein said first and second filter are positioned adjacent each other, comprising the steps of extracting said matters sequentially such that matters are collected in said first and second filters while travelling through said tortuous path through the pores of said first filter, then through the pores of said second filter.

53. The method of claim 51 further comprising the step of flushing the entire suctioning system to further eliminate the effect of suck-back phenomenon.

54. The method of claim 51 further comprising
placing a rubber dam around one or more teeth of an individual;
attaching the outlet end of the housing to a suction line of a suction system and pump;
affixing the aspirator tip to the inlet end of the housing;
supplying suction to the outlet end of the housing from the suction line of the suction system and pump;
removing amalgam from an area in close proximity to the one or more teeth of the individual;
causing the amalgam to pass through the aspirator tip, then into and through the one way anti-retraction valve;
using the filter to prevent the amalgam from passing through material of the filter;
removing the rubber dam from around the one or more teeth of the individual;
disposing of the amalgam which the filter prevented from passing through the material of the filter.

* * * * *